United States Patent
Wold et al.

(10) Patent No.: US 10,444,546 B2
(45) Date of Patent: Oct. 15, 2019

(54) OPTICAL FILTER

(71) Applicant: 3M INNOVATIVE PROPERTIES COMPANY, St. Paul, MN (US)

(72) Inventors: Chad R. Wold, Stillwater, MN (US); Michael F. Weber, Shoreview, MN (US); Myron K. Jordan, Apple Valley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/754,419

(22) PCT Filed: Sep. 20, 2016

(86) PCT No.: PCT/US2016/052580
§ 371 (c)(1),
(2) Date: Feb. 22, 2018

(87) PCT Pub. No.: WO2017/058562
PCT Pub. Date: Apr. 6, 2017

(65) Prior Publication Data
US 2018/0239171 A1 Aug. 23, 2018

Related U.S. Application Data

(60) Provisional application No. 62/236,247, filed on Oct. 2, 2015.

(51) Int. Cl.
*G02C 7/10* (2006.01)
*G02B 5/28* (2006.01)
(Continued)

(52) U.S. Cl.
CPC .............. *G02C 7/107* (2013.01); *A61F 9/022* (2013.01); *G02B 5/223* (2013.01); *G02B 5/28* (2013.01);
(Continued)

(58) Field of Classification Search
CPC ... G02B 5/26; G02B 5/28; G02B 5/20; G02B 5/23; G02C 7/104; G02C 7/107; G02C 7/105
(Continued)

(56) References Cited

U.S. PATENT DOCUMENTS 5,882,774 A 3/1999 Jonza
6,157,490 A 12/2000 Wheatley
(Continued)

FOREIGN PATENT DOCUMENTS

WO WO 2014-110101 7/2014
WO WO 2015-080908 6/2015
WO WO 2015-134255 9/2015

OTHER PUBLICATIONS

Nevitt, "Recent advances in Multilayer Polymeric Interference Reflectors", Thin Solid Films, 2013, vol. 532, pp. 106-112.
(Continued)

*Primary Examiner* — Hung X Dang
(74) *Attorney, Agent, or Firm* — Clifton F. Richardson

(57) ABSTRACT

An optical filter including a polymeric multilayer optical film is provided. The optical film has a reflection band having a reflection band edge that is, independent of location, one of a short wavelength band edge at a short wavelength side of the reflection band and a long wavelength band edge at a long wavelength side of the reflection band. The reflection band edge has a normal incidence reflection band edge wavelength that varies with location and that is a first wavelength at a first location and a second wavelength at a second location different from the first location. The first wavelength may be higher than the second wavelength by at least 2 percent.

20 Claims, 7 Drawing Sheets

(51) Int. Cl.
  *A61F 9/02* (2006.01)
  *G02B 5/22* (2006.01)
(52) U.S. Cl.
  CPC ............ *G02C 7/104* (2013.01); *G02C 7/105* (2013.01); *G02C 2202/16* (2013.01)
(58) Field of Classification Search
  USPC ......... 351/44, 159.24, 159.6, 159.65, 159.66
  See application file for complete search history.

(56) References Cited

U.S. PATENT DOCUMENTS

| | | |
|---|---|---|
| 6,531,230 B1 | 3/2003 | Weber |
| 6,783,349 B2 | 8/2004 | Neavin |
| 8,403,478 B2 * | 3/2013 | Ishak .................... G02C 7/104 351/159.29 |
| 9,739,916 B2 | 8/2017 | Weber |
| 2015/0146166 A1 | 5/2015 | Weber |

OTHER PUBLICATIONS

International Search Report for PCT International Application No. PCT/US2016/052580, dated Nov. 29, 2016, 4pgs.

\* cited by examiner

OPTICAL FILTER

BACKGROUND

Multilayer optical films may be utilized to provide a desired reflection band. The reflection and transmission characteristics of a multilayer optical film depends on incidence angle of light on the optical film. An eyewear lens may include a multilayer optical film.

SUMMARY

In some aspects of the present description, an optical filter including a polymeric multilayer optical film having a reflection band is provided. The reflection band has a first reflection band edge having a location-dependent normal incidence first reflection band edge wavelength. The first reflection band edge is, independent of location, one of a short wavelength band edge at a short wavelength side of the reflection band and a long wavelength band edge at a long wavelength side of the reflection band. The normal incidence first reflection band edge wavelength is a first wavelength at a first location and is a second wavelength at a second location different from the first location, the first wavelength higher than the second wavelength by at least 2 percent.

In some aspects of the present description, an optical filter including a polymeric multilayer optical film having a reflection band is provided. The film has a first reflection band edge wavelength for light incident on the lens at normal incidence at a first location, and has a second reflection band edge wavelength for light incident on the lens at a 25 degree incidence angle at the first location. The second reflection band edge wavelength differs from the first reflection band edge wavelength by a first percentage. The film has a third reflection band edge wavelength for light incident on the lens at a 25 degree incidence angle at a second location different from the first location, the third reflection band edge wavelength differing from the first reflection band edge wavelength by a second percentage being less than one half of the first percentage. Each of the first, second and third reflection band edge wavelengths are wavelengths of a short wavelength band edge at a short wavelength side of the reflection band or each of the first, second and third reflection band edge wavelengths are wavelengths of a long wavelength band edge at a long wavelength side of the reflection band.

In some aspects of the present description, an optical filter including a polymeric multilayer optical film having a reflection band is provided. When an incidence position of a light ray that is incident on an outer surface of the lens in air and that passes through a fixed point proximate the lens opposite the outer surface varies through a portion of the outer surface such that an incidence angle of the light ray with the outer surface varies from zero degrees to 25 degrees, the optical filter provides a reflection band edge wavelength having a first maximum variation of less than 2.5 percent.

DETAILED DESCRIPTION

Figure 1:
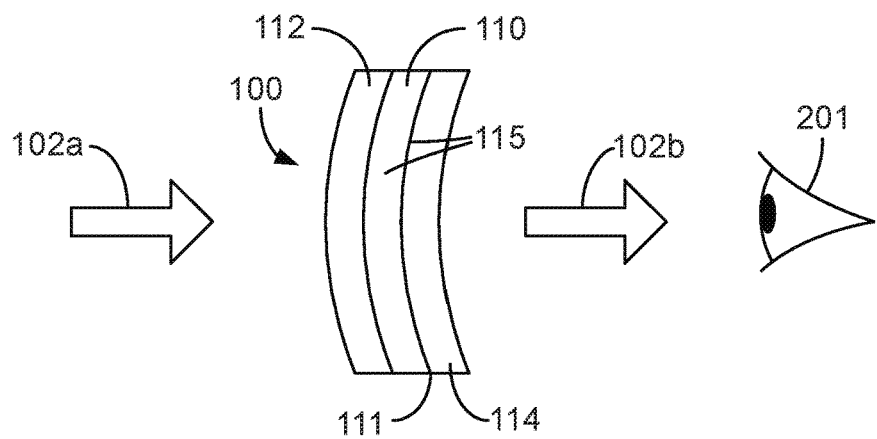
FIG. 1 is a schematic side view of an optical lens filtering light observed by an individual.

In the following description, reference is made to the accompanying drawings that forms a part hereof and in which various embodiments are shown by way of illustration. The drawings are not necessarily to scale. It is to be understood that other embodiments are contemplated and may be made without departing from the scope or spirit of the present disclosure. The following detailed description, therefore, is not to be taken in a limiting sense.

Optical filters that include polymeric multilayer optical films can be incorporated into eyewear lenses to provide desired reflection and transmission characteristics. In some cases, it is desired to block specific wavelengths of light. Such blocking can be accomplished by using a polymeric multilayer optical film that provides a reflection band in the wavelengths that are desired to be blocked. Such polymeric multilayer optical films may be described as interference filters since such films are typically based on constructive or destructive interference of light at interfaces of (typically) tens, hundreds, or thousands of individual microlayers in one or more layer stacks. The optical filters of the present description may be incorporated into lenses. The optical filter may include a polymeric multilayer interference filter and in some cases may further include one or more absorptive layers that may be included to reduce glare by absorbing in selected wavelengths, for example. In some embodiments, the eyewear lenses may have an optical power and may be used as prescription lenses. In other embodiments, the eyewear lenses have substantially no optical power and may be used, for example, in protective eyewear (e.g., safety glasses, goggles, face-shields (e.g., face-shields for laboratory use or face-shields incorporated into a helmet, and the like) or may be used primarily for the optical effects provided by the polymeric multilayer optical film in the eyewear lenses. The optical effects provided by the eyewear lenses of the present description may be useful in a variety of applications, including for example, color blind correction filters, blue edge filters, laser light blocking filters, and head-mounted displays where the lens may be used to alter or redirect light incident on the lens from an image source (e.g., projector).

The optical filters may also be used in applications other than eyewear lenses. For example, in machine vision systems, which may include one or more optical detectors (e.g., electronic detector eyes), it may be desired to utilize one or more transmission bands (e.g., to focus on a part with a specific color) and it may be desired that the transmission band(s) do not shift for light transmitted to an optical sensor from different directions. The optical filters of the present description may be utilized to provide such fixed transmission band(s). This can be done by utilizing a multilayer optical film with reflection bands surrounding the desired transmission band(s) and optionally using additional absorbing filters (e.g., dyes which may be coated onto the multilayer optical film) to absorb at least some portion of the light reflected from the reflection bands. In this way, a suitable band-pass filter can be provided. The filter may be symmetric (e.g., shaped as a spherical cap centered on the electronic eye with a thickness that varies with radial distance from a center of the spherical cap) or may be asymmetric.

Figure 15:
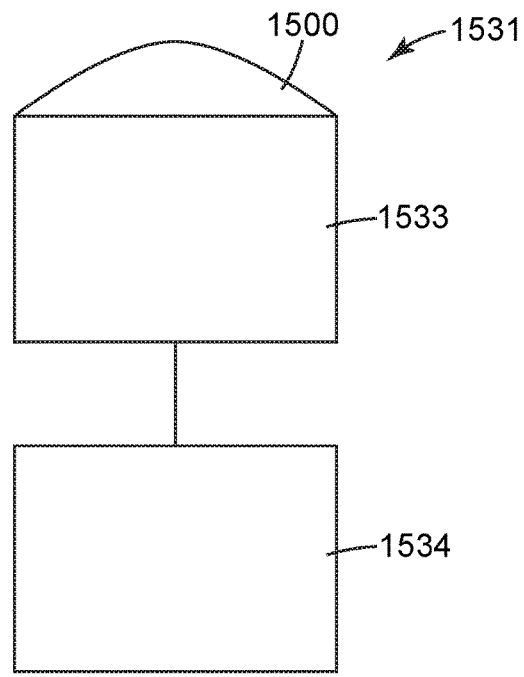
FIG. 15 is a schematic illustration of a machine vision system.

An exemplary machine vision system is schematically illustrated in FIG. 15 which shows machine vision system 1531 including an optical detector 1533 having a lens 1500 that includes any of the optical filters of the present description. Machine vision system 1531 also includes a computer system 1534 adapted to receive (via one or more wired or wireless connections) image data from the optical detector 1533. The computer system 1534 may be adapted to control one or more process parameters, for example, based on data received from the optical detector 1533.

In some embodiments, the optical filter provides a reflection band that is reflective for light having a first polarization state and for light having a second orthogonal polarization state. In other embodiments, the optical filter may be a reflective polarizer which is reflective for light having a first polarization state (e.g., a linear polarization along a first axis) and is not reflective for light having an orthogonal second polarization state (e.g., a linear polarization along a second axis orthogonal to the first axis). In some embodiments, the optical filter is a notch filter which provides one or more reflection bands having full width at half maximum at normal incidence of no more than 100 nm, or no more than 60 nm, or no more than 50 nm, or no more than 40 nm.

An example of a suitable application of an optical filter of the present description is in color blind correction filters such as those described in PCT Publication No. WO 2014/110101 (Wold et al.), which is hereby incorporated herein by reference to the extent that it does not contradict the present description. Such optical filters typically include a polymeric multilayer optical film having a reflection band at a design angle of incidence (e.g., normal incidence) that includes 550 nm and that has a full width at half maximum (FWHM) of 60 nm or less. Such reflection bands have been found to be useful in helping color vision deficiency (CVD) individuals better distinguish or discriminate colors. However, the reflection band of a polymeric multilayer optical film depends on incidence angle and when a conventional polymeric multilayer optical film is included in eyewear lens, the resulting reflection band depends on the eye viewing direction through the film. This is because conventional polymeric multilayer optical films have a uniform thickness and the light passing through the film at a non-normal incidence will have a greater path length through the film than the thickness of the film. Typical conventional polymeric multilayer optical films exhibit a rapid spectral shift with angle of incidence due to the relatively low refractive indices of polymeric materials compared to metal-oxide film stacks or metal-oxide/thin metal stacks made by vacuum deposition. Conventional polymeric multilayer optical films exhibit particularly large reflection band shifts when used in wrap-around style eyewear lenses, such as those used as protective lenses, for example, and when used in eyewear lenses having radii of curvature of 100 mm or less, for example.

According to the present description, it has been found that the thickness of polymeric multilayer optical films can be made to vary in such a way that when the film is incorporated into eyewear lens, the film provides a reflection band that has a much reduced or even substantially eliminated dependence on eye viewing direction as compared to conventional films. Having a reflection band that does not shift significantly with eye viewing direction is useful in applications, such as the color blind correction filters, where a specific narrow wavelength band is desired. As described further elsewhere herein, the desired thickness variation in the optical films can be achieved using thermoforming techniques to stretch the film in a controlled non-uniform manner. Using a variable thickness polymeric multilayer optical film allows the optical film to be effectively used in eyewear lenses having high curvatures. For example, in some embodiments, an eyewear lens according to the present description may have a radius of curvature of less than about 100 mm.

In some embodiments, a polymeric multilayer optical film suitable for use in CVD corrective eyewear lenses has, at one or more locations and at normal incidence, a reflection band that has a width (FWHM) of 60 nm or less, or 40 nm or less, the polymeric multilayer optical film has an average internal transmission from 420-680 nm of at least 30 percent or of at least 50%, and at least one portion of the film has at normal incidence an average internal transmission of 10% or less, or of 5% or less, or of 2% or less, or of 1% or less over a 10 nm wide wavelength range that includes 550 nm and is associated with the reflection band. When used in CVD eyewear lenses, it may be desired for the internal transmission over the 10 nm wide wavelength range that includes 550 nm to be as small as possible and the internal transmission over this 10 nm wide wavelength range even be substantially zero. The reflection band width (FWHM) may be in a range of 20 nm to 60 nm, or of 20 nm to 50 nm, or of 20 nm to 40 nm.

In some embodiments, when the incidence angle of a light ray with the outer surface on an eyewear lens including the optical film varies from zero degrees to 25 degrees, or to 30 degrees and intersects a fixed point proximate the lens opposite the outer surface, a wavelength of 550 nm remains in the reflection band and a width (FWHM) of the reflection band remains no more than 60 nm, or no more than 40 nm. The optical film may also include a dye layer disposed toward a viewer side of the film in order to reduce glare, for example. The reflection band width (FWHM) may remain in a range of 20 nm to 60 nm, of 20 nm to 50 nm, or of 20 nm to 40 nm.

In some embodiments, the eyewear lens includes a polarizer in addition to the CVD correcting polymeric multilayer optical film. It has been found that including a polarizer can enhance the CVD correcting effect. The polarizer may be a reflective polarizer, an absorbing polarizer, or a multilayer optical stack including both a reflective polarizer and an absorbing polarizer with the block axes of the polarizers aligned.

Another example of an application where a reflection band is desired is blue edge filters such as those described in US Pat. Pub. No. 2015/0146166 (Weber et al.), which is hereby incorporated herein by reference to the extent that it does not contradict the present description. Such filters, which may be or may include a polymeric multilayer optical film, may be used in corrective lenses and/or sunglasses in order to reduce harmful effects of shorter wavelength light (e.g., violet and/or ultraviolet (UV) and/or near ultraviolet light). The phrase "blue light" refers to light having a wavelength in a range from 400 to 500 nm. The phrase "violet light" refers to light having a wavelength in a range from 400 to 420 nm. The phrase "ultraviolet light" refers to light having a wavelength of less than 400 nm or in a range from 100 to 400 nm and "near ultraviolet light" refers to light having a wavelength in a range from 300 to 400 nm. According to the present description, the thickness profile of a polymeric multilayer optical film may be tailored so that the film provides a blue edge filter with a band edge that depends only weakly or substantially not at all on the eye viewing direction through an eyewear lens that includes the polymeric multilayer optical film.

In some embodiments, a polymeric multilayer optical film suitable for use in eyewear lenses creates a sharp band edge to provide for quick transitions from low to high transmission of light as a function of wavelength. The polymeric film or polymeric interference filter can be an infrared reflecting film having a higher order harmonic reflecting a band of blue light. The eyewear lens can block (transmission is less than 10%) blue light up to 440 nm and transmit (transmission is greater than 50%) blue light greater than 460 nm or 450 nm. A band of yellow light can be blocked to improve the white balance of the light transmitted through the lens. A UV absorber can be included to block 400 nm or lower light wavelengths. In some embodiments the polymeric multilayer optical film reflects a band of yellow light. In some embodiments the polymeric multilayer optical film may be a bandstop filter that reflect a bands of visible or yellow light having a FWHM of less than 40 nm, and a 1% floor of the reflected band of visible or yellow light may have a width greater than 20 nm or greater than one half the FWHM value. The width of the 1% floor is the maximum range of wavelengths over which the average transmission of the reflection band is less than 1%.

In some embodiments, the polymeric multilayer optical film has a long wavelength band edge, and for at least some portions of the polymeric multilayer optical film, the long wavelength band edge is in a range from 420 to 440 nm at normal incidence. The polymeric multilayer optical film may have an average light transmission of less than 2% at normal incidence across the reflection band and may transmit at least 80 percent of blue light having a wavelength that is 10 nm or greater than the long wavelength band edge at normal incidence. In some embodiments, the reflection band has a short wavelength band edge and a long wavelength band edge, and for at least some portions of the polymeric multilayer optical film at normal incidence, the short wavelength band edge is at about 400 nm or less, the long wavelength band edge is in a range from 420 to 440 nm, and the polymeric multilayer optical film has an average light transmission of less than 2% across the reflection band and may transmit at least 80 percent of blue light having a wavelength that is 10 nm or greater than the long wavelength band edge.

Another example of an application where a reflection band is desired is optical films used to reduce circadian rhythm disruptions such as those described in U.S. patent application Ser. No. 14/220,193 (Weber et al.), filed on Mar. 20, 2014, which is hereby incorporated herein by reference to the extent that it does not contradict the present description. Suitable polymeric multilayer optical films for use as a circadian rhythm film may include a polymeric bandstop filter having a short wavelength band edge and a long wavelength band edge and reflecting a band of blue light in a range from 440 nm to 480 nm and transmitting greater than 50% of blue light at a wavelength of 10 nm longer than the long wavelength band edge and at a wavelength of 10 nm shorter than the short wavelength band edge. According to the present description, the thickness profile of the polymeric multilayer optical film may be tailored so that the film provides a bandstop filter with band edges that depends only weakly or substantially not at all on the eye viewing direction through an eyewear lens that includes the polymeric multilayer optical film.

Another type of eyewear lenses where the polymeric multilayer optical films of the present description are useful is protective eyewear lenses that block a certain wavelength range that may be hazardous to an individual. For example, laser protective eyewear is used to block laser light. It is typically desired for the eyewear to block at least certain wavelengths (corresponding to the wavelength(s) produced by the laser) over a full range of view angles. In some embodiments, at least a portion of the polymeric multilayer optical film at normal incidence reflects at least 80 percent of infrared light in a wavelength range of 1025 nm to 1100 nm, or 793 nm to 1064 nm, or 770 nm to 1200 nm, or 760 nm to 1300 nm, or 760 nm to 1330 nm. In some embodiments, eyewear lens including the polymeric multilayer optical film blocks at least 80 percent of infrared light in a wavelength range of 1025 nm to 1100 nm, or 793 nm to 1064 nm, or 770 nm to 1200 nm, or 760 nm to 1300 nm, or 760 nm to 1330 nm throughout eye viewing directions from minus to plus 30 degrees. Such eyewear lenses are useful for blocking light from various laser light sources. For example, it may be desired to block light from a neodymium-doped yttrium aluminum garnet (Nd:YAG) laser which produces wavelengths of about 1064 nm. It may also be desired for a protective eyewear lens to block light from various laser diodes. Wavelengths of light from laser diodes include 793 nm, 808 nm, 830 nm, 905 nm, and 980 nm. Accordingly, in some cases it may be desirable to block light at least from 793 nm to 1064 nm.

In some embodiments, the polymeric multilayer optical film provides a long wavelength band edge that is greater than 1064 nm throughout eye viewing directions from minus to plus 25 degrees or 30 degrees when the optical film is included in an eyewear lens. In some embodiments, the polymeric multilayer optical film provides a reflection band having a long wavelength band edge wavelength at normal incidence that is greater than 1064 nm, or greater than 1100 nm, or greater than 1200 nm in at least some locations of the optical film. In some embodiments, when the incidence angle of a light ray with the outer surface on an eyewear lens including the optical film varies from zero degrees to 25 degrees, or to 30 degrees and intersects a fixed point proximate the lens opposite the outer surface, the optical film provides a reflection band having a long wavelength band edge that remains greater than 1064 nm, or greater than 1100 nm, or greater than 1200 nm. In some embodiments, the polymeric multilayer optical film provides a reflection band having a short wavelength band edge wavelength at normal incidence that is less than 793 nm, or less than 780 nm, or less than 770 nm, or less than 760 nm in at least some locations of the optical film. In some embodiments, the optical film has a reflection band that, at normal incidence, includes wavelengths at least in a range of 793 nm to 1064 nm in at least some locations of the optical film. In some embodiments, when the incidence angle of a light ray with the outer surface on an eyewear lens including the optical film varies from zero degrees to 25 degrees, or to 30 degrees and intersects a fixed point proximate the lens opposite the outer surface, wavelengths at least in a range of 793 nm to 1064 nm remain in the reflection band. In some embodiments, at least a portion of the polymeric optical film at normal incidence reflects at least 80 percent of infrared light in a wavelength range of 793 nm to 1064 nm, or in a range of 770 nm to 1200 nm, or in a range of 760 nm to 1300 nm, for example.

FIG. 1 is a schematic diagram side view of an eyewear lens 100 filtering light observed by an individual 201. The eyewear lens 100 includes first and second substrates 112 and 114 and a polymeric multilayer optical film 110 disposed on the substrates. The polymeric multilayer optical film 110 together with optional dye material 111 forms optical filter 115. While the polymeric multilayer optical film 110 is illustrated separating a first substrate 112 from a second substrate 114, it should be understood that the polymeric multilayer optical film 110 can be disposed on only one substrate, as desired. In addition, it should be understood that an adhesive can fix the polymeric multilayer optical film 110 to either or both of the first substrate 112 and second substrate 114. The substrates 112 and 114 can be spherically curved as are typically utilized in eyewear for corrective lenses or for sunglasses, for example, or any other suitable geometry may be used.

The first and/or second substrates 112 and 114 may be curved polymeric substrates (for example, formed from polycarbonate) that can be formed by injection molding at elevated temperatures of, for example, 150 degrees centigrade or higher. The first and/or second substrates may have a thickness of at least 0.5 mm, or at least 1 mm, or at least 2 mm. In some cases, the first and second substrates 112 and 114 may be formed individually and then the optical film 110 laminated between the first and second substrates 112 and 114. In some cases, an optical film may be laminated between two polymeric sheets (for example, polycarbonate sheets having a thickness of 0.25 mm to 2 mm) and then the curved lens 100 can be formed from the laminate using a thermoforming process. In some cases, an optical film may be laminated between two thin polymeric sheets (for example, polycarbonate sheets having a thickness of about 0.25 mm) and a thermoforming process can be utilized to form a curved "wafer" that includes the optical film. The thermoforming process may include shaping the laminate by sagging into a mold at elevated temperatures. An additional injection molding step can then be utilized to add additional polymeric layers (e.g., thicker polycarbonate layers) to one or both sides of the curved wafer resulting in a curved lens. As discussed elsewhere herein, the thermoforming process can be adapted to selectively stretch the optical film so that the resulting film has a variable thickness and a reflection band that has little or substantially no dependence on eye viewing direction as compared to conventional films.

The polymeric multilayer optical film 110 receives incident light 102a and filters selected wavelengths of the light to provide filtered light 102b. The filtered light 102b is perceived by the eyes of an individual 201. The effect of the polymeric multilayer optical film 110 may be to block undesired light while simultaneously providing a desired color balanced white transmission. The polymeric multilayer optical film 110 may be described as a polymeric interference filter and may block undesired light by providing one or more reflection bands.

The lens 100 may optionally include a dye material 111 which may be a coating applied to a surface of the polymeric multilayer optical film 110 or may be an additional layer included in or added to the polymeric multilayer optical film 110. The dye material 111 can be disposed between the polymeric multilayer optical film 110 and the substrate 114. In some embodiments the dye material 111 is disposed between the polymeric multilayer optical film 110 and the observer 201. This is useful to reduce glare if the polymeric multilayer optical film 110 includes a narrow reflection band for light having wavelengths absorbed by the dye material.

In some embodiments, the dye material 111 is a magenta layer. Suitable magenta dyes include Epolight™ 5391 Visible Light Dye, sold by Epolin, Inc., Newark, N.J. Other suitable magenta dyes and layers are described in PCT Publication No. WO 2014/110101 (Wold et al.). In some embodiments, the dye material 111 may be a yellow light absorbing material that absorbs light mainly within a wavelength range from 560 to 600 nm. Useful yellow light absorbing dyes include Epolight™ 5819 from Epolin Corporation and dyes ABS 584 and ABS 574 from Exciton Corp. The Epolight 5819 and the Exciton ABS 584 have absorption peaks near 584 nm and the ABS 574 has a peak absorption near 574 nm.

Figure 2:
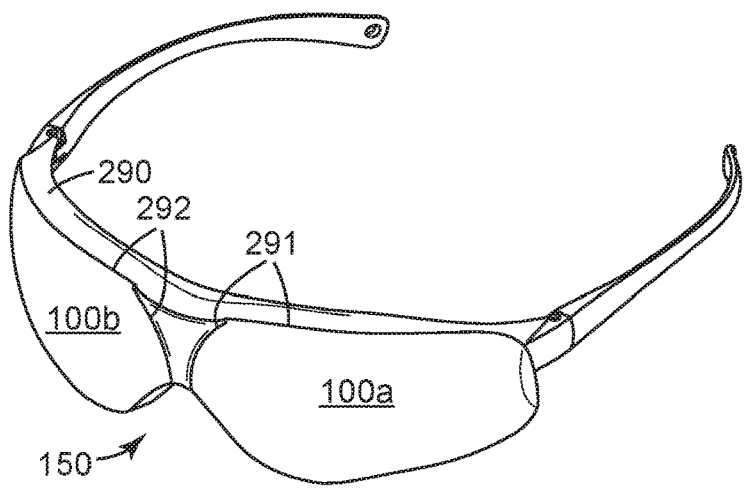
FIG. 2 is a perspective view of illustrative eyewear utilizing the eyewear lenses described herein.

FIG. 2 is a perspective view of illustrative eyewear 150 utilizing first and second eyewear lenses 100a and 100b, each of which may correspond to any of the eyewear lens described herein (e.g., eyewear lens 100 of FIG. 1). Eyewear 150 includes a frame 290 having a first lens mounting portion 291 and a second lens mounting portion 292 proximate the first lens mounting portion 291. The first eyewear lens 100a is mounted on the first lens mounting portion 291 and the second eyewear lenses 100b is mounted at the second lens mounting portion 292. It is understood that the eyewear 150 can have any useful configuration.

In other embodiments, eyewear lenses 100a and 100b may be replaced with display systems which include an optical filter of the present description, and eyewear 150 may be a head mounted display system which may be a virtual reality or an augmented reality system. In still other embodiments, eyewear lens 100a may extend over both eye positions and eyewear lens 100b may be omitted (e.g., in goggles or face-shield applications).

Figure 3:
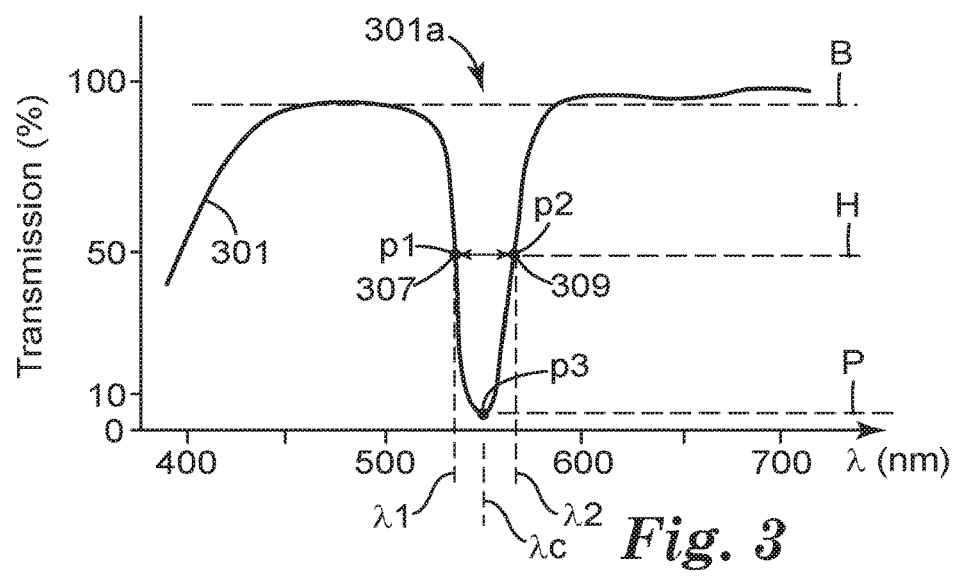
FIG. 3 is a graph of the transmission spectrum of a hypothetical optical filter.

FIG. 3 is a graph of the transmission spectrum of a hypothetical optical filter or of one or more components thereof such as a multilayer optical film. The hypothetical filter may be a polymeric interference filter (e.g., a polymeric multilayer optical film as described herein) or a combination of a polymeric interference filter with a dyed layer or other filter. In this figure, percent transmission is plotted against optical wavelength λ, in nanometers, the wavelength axis extending over the range from 400 to 700 nm, which is sometimes treated as the human visible wavelength range. The curve 301 may represent the measured transmission of the entire filter, or of one or more individual components thereof, at normal incidence or another design angle of incidence. Without loss of generality, for the remainder of the discussion of FIG. 3, it will be assumed for simplicity that the curve 301 represents the transmission of the entire filter (note however that the filter may in some cases be only a polymeric multilayer optical film). The illustrated filter selectively blocks light within a narrow band in a portion of the green region of the visible spectrum, evidenced by the low transmission of the rejection band 301a of the curve 301. The rejection band 301a may be provided as a reflection band of a polymeric multilayer optical film or as a combination of a reflection band of a polymeric multilayer optical film and an absorption band of one or more absorptive layers included in the filter in addition to the polymeric multilayer optical film.

In order to quantify relevant features of the curve 301, a baseline value B of the curve 301, a peak value P of the curve 301 (in this case the peak value P corresponds to a transmission minimum for the rejection band 301a, shown at point p3), and an intermediate value H of the curve 301, halfway between P and B are identified in FIG. 3. The curve 301 intersects with the value H at the points p1 and p2. These points lie on the short wavelength band edge 307 and the long wavelength band edge 309, respectively, of the rejection band 301a and define the short wavelength band edge wavelength $\lambda 1$ and the long wavelength band edge wavelength $\lambda 2$. The short and long wavelength band edge wavelengths can be used to calculate two other parameters of interest: the width (full width at half-maximum, or "FWHM") of the rejection band 301a, which equals $\lambda 2-\lambda 1$; and the center wavelength $\lambda c$ of the rejection band 301a, which equals $(\lambda 1+\lambda 2)/2$. Note that the center wavelength $\lambda c$ may be the same as or different from the peak wavelength (see point p3) of the rejection band 301a, depending on how symmetrical or asymmetrical the rejection band 301a is.

The transmission of a polymeric multilayer optical film or of an optical filter (or component(s) thereof) refers generally to the transmitted light intensity divided by the incident light intensity (for light of a given wavelength, incident direction, etc.), but may be expressed in terms of "external transmission" or "internal transmission". The external transmission of an optical element is the transmission of the optical element when immersed in air, and without making any corrections for Fresnel reflections at the air/element interface at the front of the element or for Fresnel reflections at the element/air interface at the back of the element. The internal transmission of an optical element is the transmission of the element when the Fresnel reflections at its front and back surfaces have been removed. The removal of the front and back Fresnel reflections may be done either computationally (e.g. by subtracting an appropriate function from the external transmission spectrum), or experimentally. For many types of polymer and glass materials, the Fresnel reflections are about 4 to 6% (for normal or near-normal angles of incidence) at each of the two outer surfaces, which results in a downward shift of about 10% for the external transmission relative to the internal transmission. FIG. 3 does not specify which of these transmissions is used, hence, it may generally apply to either internal or external transmission. If transmission is referred to herein without being specified as internal or external, it may be assumed that the transmission refers to external transmission, unless otherwise indicated by the context. In many eyewear lenses, the application of surface anti-reflection coatings may result in Tinternal Texternal.

In some embodiments, a polymeric multilayer optical film may have a reflection band having a maximum reflection (e.g., at point p3 in FIG. 3) of at least 60%, or at least 70%, or at least 80% (or a minimum transmission that is less than 40%, or less than 30%, or less than 20%). In some cases, the internal transmission through the optical film may be at least 60%, or at least 70%, or at least 80% in regions on either side of the reflection band. For example, in some embodiments, the optical film may have a minimum internal transmission in the reflection band of less than 20% and may have an internal transmission of at least 80% at a wavelength 10 nm shorter, or 20 nm shorter, than a short wavelength band edge of the reflection band, and/or the optical film may have an internal transmission of at least 80% at a wavelength 10 nm longer, or 20 nm longer, than a long wavelength band edge of the reflection band.

Multilayer polymeric optical films described herein can be fabricated to reflect various bands of ultraviolet, visible and/or infrared light, for example. The reflective optical films can be made by a continuous process of coextrusion of alternating low and high index polymeric materials and stretching the resulting multilayer polymer web, e.g. as described in U.S. Pat. No. 5,882,774 (Jonza et al.), U.S. Pat. No. 6,531,230 (Weber et al.), and U.S. Pat. No. 6,783,349 (Neavin et al.). The layer thickness profiles may be tailored to provide a multilayer optical film that operates as a narrow band reflector, for example, whereby light within the narrow band of wavelengths is highly reflected (with correspondingly low transmission) and light outside of the narrow band of wavelengths is highly transmitted (with correspondingly low reflection). In some cases a narrow reflection band with sharp band edges is desired. In other cases, a broad reflection band (e.g., an infrared band) may be desired with a sharp band edge (e.g., the band edge between visible light wavelengths where the film may be transmissive and infrared wavelengths where the film may be reflective). In order to obtain sharpened band edges, the layer thickness profiles may be graded similar to those discussed in U.S. Pat. No. 6,157,490 (Wheatley et al.), and higher order harmonic bands were used as described in U.S. Pat. No. 6,531,230, as well as in the publication by T. J. Nevitt and M. F. Weber "Recent advances in Multilayer Polymeric Interference Reflectors" in Thin Solid Films 532 (2013) 106-112.

Multilayer optical films having a narrow reflection band can be made by co-extruding polymer resin layers so as to form relatively narrow reflection bands. The use of highly birefringent materials such as a polyester, in combination with a low refractive index material such as an acrylic, provide for useful refractive index differences between alternating layers which then provide for high reflectivity in the reflection band. Several options exist for making these reflectors. In some cases, the layer thickness profile of the microlayers can be tailored to provide a first-order reflection band (at normal incidence) at a desired visible wavelength. In other cases, the microlayers can be made thicker such that the first-order reflection band at normal incidence is at an infrared wavelength, but a high order harmonic (e.g., a $2^{nd}$, $3^{rd}$, or $4^{th}$ order harmonic) of the infrared band is at the desired visible wavelength. This latter design approach, and subsequent polymer processing techniques, are discussed in U.S. Pat. No. 6,531,230 (Weber et al.).

Assuming relatively small index differentials, such as those available with polymeric reflectors, the reflective power of a given reflectance order of a multilayer stack is inversely proportional to the order number, and it depends greatly on the f-ratio (defined below). The reflective power of a given harmonic band of a multilayer interference reflector is defined as the area under the optical density spectrum of the given band, i.e. the area under the spectral curve of −Log(T) vs. wavelength, normalized for wavelength and after removal of the effects of reflection at the polymer air surfaces (surface reflections may be approximately 12% (6% for each surface) for out-of-band wavelengths when polyethylene terephthalate (PET) skin layers are present). For narrow band reflectors, the various higher order harmonics do not overlap and each order has a distinct reflection band and the reflective power can easily be measured. Thus, depending on the number of layers and the materials that one desires to use in the reflector, a given higher order band may not have high enough reflective power to provide the desired reflectivity for a given wavelength range. In that case a lower order reflective band can be used, although the band edges may not be as sharp, i.e. as steep, as a higher order band. The limiting sharpness, or slope of a band edge is inversely proportional to the intrinsic bandwidth (IBW) of a quarterwave stack, which is well known in the art to be given by IBW=Sin$^{-1}$[($n_h$−$n_l$)/($n_h$+$n_l$)] or simply IBW≈($n_h$+$n_l$) for small index differentials.

For the various higher order harmonic reflection bands, the effective index differential, and therefore the IBW, is reduced by the absolute value of Sin[n*Pi*f]/n where n is the order number and f is the f-ratio.

A 1$^{st}$ order reflection band of a given thickness graded multilayer stack can have the same band edge slope as a third order reflection band of a second material stack if the index differential of the former is one third that of the latter. Alternatively, the effective index differential of a given high and low index material pair can be reduced simply by changing the f-ratio of the layer pair.

The f-ratio of an interference stack is given by f-ratio= ($n_h$*$d_h$)/($n_h$*$d_h$+$n_l$*$d_l$) where $n_h$ and $n_l$ are the values of the high and low indices of refraction of a layer pair in the stack and $d_h$ and $d_l$ are their thicknesses. Note that in a stack having a graded layer thickness distribution, the low and the high index layer thickness distributions should be graded equally in order to maintain a constant f-ratio throughout the stack.

With 275 layers of PET and coPMMA (co-polymethyl methacrylate), there is sufficient reflective power in the 3rd, 4th and 5th order harmonic bands. Thus, sharper band edges and acceptable reflectivity and bandwidth are generally achievable with several of the higher order bands of PET/coPMMA multilayers that can be fabricated with equipment that is known in the art. The use of higher order bands to achieve sharp band edges with inorganic vapor deposited quarter wave stacks is in general very rare for two reasons: the large index differential of the inorganic material pairs with the subsequent low number of layers produces wide bands with relatively low sloped band edges, and the different approach to stack design wherein automatic computerized stack design prescribes the thickness of each layer using a search algorithm which returns a seemingly random variation of layer thickness. In the latter case, it is difficult to say whether the stack is of any given order, although many thickness values are near the first order values. In addition, the deposition of inorganic coatings typically require high substrate temperatures. Furthermore, the coating cannot be subsequently thermoformed along with the substrate, i.e., the coating must be applied to individual lenses after they are formed to the desired curvature. A uniform coating is difficult to achieve on a curved substrate, particularly a spherically curved substrate, especially in mass production onto large arrays of lenses.

Figure 4:
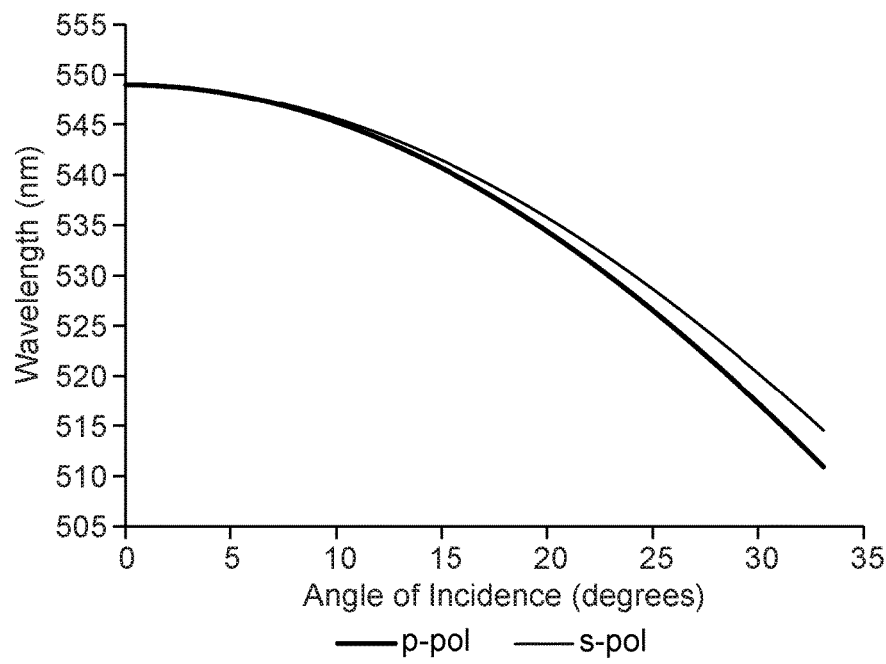
FIG. 4 is a graph of a reflection band center wavelength of a polymeric multilayer optical film as a function of incidence angle.

FIG. 4 is a graph of a reflection band center wavelength versus incidence angle for a polymeric multilayer optical film having a reflection band center wavelength of about 549 nm. The reflection band also has first and second band edge wavelengths at short and long wavelength band edges, respectively. The graph shows the reflection band center wavelength for s-polarized and for p-polarized incident light. The center wavelength differs for the two polarization states at large angle of incidence and are approximately the same for smaller incidence angles. As used herein, unless specified differently, the reflection band edge wavelengths and the reflection band center wavelengths refer to an average of the values for s- and p-polarization. When included in an eyewear lens, the shifts in reflection band edge or center wavelengths with incidence angles translates into shifts in reflection band edge or center wavelengths with eye viewing angle through the eyewear lens. Optical filters described herein which include a multilayer optical film can at least partially compensate for this shift in reflection band edge or center wavelengths with eye viewing angle by tailoring the thickness of the multilayer optical film with position in the eyewear lens.

Figure 5:
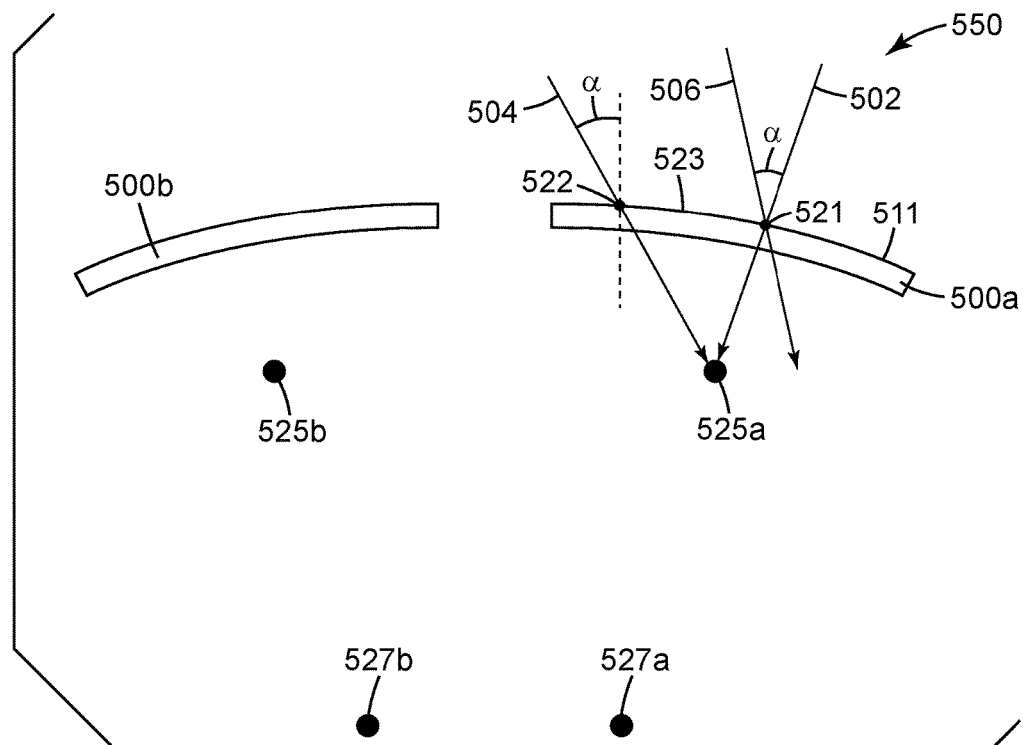
FIG. 5 is a schematic diagram of a lens geometry.

FIG. 5 is a schematic diagram of a lens geometry showing first and second lenses 500a and 500b disposed in an optical system 550 which may be suitable for use in eyewear (e.g. glasses or goggles or a head mounted display system such as a virtual reality or augmented reality system). First lens 500a includes first and second locations 521 and 522 and an outer surface 511 having a portion 523 between first and second locations 521 and 522. Light ray 502 in incident on first location 521 of lens 500a at normal incidence and passes through a fixed point 525a proximate the lens 500a opposite the outer surface 511 of the lens 500a. A corresponding fixed point 525b for second lens 500b is also illustrated in FIG. 5. Fixed points 525a and 525b may correspond to centers of rotation of right and left eyes, respectively, when eyewear containing first and second lens 500a and 500b is worn. Also illustrated in FIG. 5 are first and second centers of curvature 527a and 527b of the first and second lenses 500a and 500b, respectively. Light ray 504 is incident on a second location 522 of lens 500a at an incidence angle α and passes through the fixed point 525a. Light ray 506 is incident on the first location 521 at the same incidence angle α. The incidence angle α may be 20 degrees, or 25 degrees, or 30 degrees, for example.

It may be desired that the transmission properties of the lens 500a for light ray 504 be substantially the same as for light ray 502. For example, it may be desired that a polymeric multilayer optical film included in lens 500a have a reflection band with a first band edge, a second band edge, and/or a reflection band center wavelength that is the same or about the same for light rays 502 and 504. However, if the polymeric multilayer optical film has a constant thickness throughout the lens 500a, then light ray 504 will experience a shifted reflection band compared to light ray 502. According to some aspects of the present description, the polymeric multilayer optical film may have a variable thickness that compensates for this shift. As a result of the variable thickness, the optical film may have a normal incidence short wavelength band edge wavelength (corresponding to λ1 in FIG. 3, for example), a normal incidence long wavelength band edge wavelength (corresponding to λ2 in FIG. 3, for example), and/or a normal incidence reflection band center wavelength (corresponding to λc in FIG. 3, for example) that varies with position. However, the band edge(s) and/or center wavelengths at the actual incidence angles of light passing through the first lens 500a and intersecting fixed point 525a, may be approximately independent of position on the first lens 500a.

In some embodiments, the polymeric multilayer optical film has a reflection band (corresponding to band 301a in FIG. 3, for example) having a first reflection band edge having a normal incidence first reflection band edge wavelength. The normal incidence first reflection band edge wavelength is location dependent. That is, the normal incidence first reflection band edge wavelength depends of position along a surface of the optical film or along the outer surface 511 of eyewear lens 500a, for example. The first reflection band edge is, independent of location, one of a short wavelength band edge (corresponding to short wavelength band edge 307 in FIG. 3, for example) at a short wavelength side of the reflection band and a long wavelength band edge (corresponding to long wavelength band edge 309 in FIG. 3, for example) at a long wavelength side of the reflection band. The normal incidence first reflection band edge wavelength is a first wavelength at the first location 521 and is a second wavelength at the second location 522. The first wavelength may be higher than the second wavelength by at least 2 percent, or at least 3 percent, or at least 4 percent, or at least 5 percent, and in some cases may be higher than the second wavelength by no more than 10 or 15 or 20 percent. The shift in normal incidence reflection band wavelengths with location may be tailored by varying the thickness of the optical film with location to compensate for shifts in reflection band wavelengths with eye viewing direction that would otherwise occur when the optical film is incorporated into an eyewear lens.

The reflection band may also have a second reflection band edge having a normal incidence second reflection band edge wavelength and may have a reflection band center wavelength that is the arithmetic mean of the first and second band edge wavelengths. However, in some cases it may be difficult to observe both a short and long wavelength band edge of the polymeric multilayer optical film due to dyes or other absorbing layers included with the polymeric multilayer optical film. For example, the polymeric multilayer optical film may provide a reflection band near UV wavelengths and only the long wavelength reflection band edge of the polymeric multilayer optical film may be readily observable due to shortwave absorption of a PEN layer or of a UV absorbing dye.

In some embodiments, the reflection band has a normal incidence reflection band center wavelength (corresponding to center wavelength $\lambda c$ in FIG. 3) that is higher at first location 521 than at the second location 522 by at least 2 percent, or at least 3 percent, or at least 4 percent, or at least 5 percent, and in some cases the normal incidence reflection band center wavelength is higher at first location 521 than at the second location 522 by no more than 10 or 15 or 20 percent.

In some embodiments, the optical film has a first reflection band edge wavelength for light 502 incident on the lens at normal incidence at a first location 521, and has a second reflection band edge wavelength for light 506 incident on the lens at an incidence angle $\alpha$, which may be 25 degrees, at the first location 521. The second reflection band edge wavelength may differ from the first reflection band edge wavelength by a first percentage. The optical film has a third reflection band edge wavelength for light incident on the lens at an incidence angle $\alpha$ at the second location 522. The third reflection band edge wavelength may differ from the first reflection band edge wavelength by a second percentage which may be less than one half (or less than one third or less than one fourth or less than one fifth) of the first percentage.

As used herein, a second quantity may be said to differ from a first quantity by a percentage given by the absolute value of the difference between the first and second quantities divided by the absolute value of the first quantity. Each of the first, second and third reflection band edge wavelengths are wavelengths of a short wavelength band edge at a short wavelength side of the reflection band (corresponding to short wavelength band edge 307 in FIG. 3, for example) or each of the first, second and third reflection band edge wavelengths are wavelengths of a long wavelength band edge at a long wavelength side of the reflection band (corresponding to long wavelength band edge 309 in FIG. 3, for example).

In some embodiments, the first percentage is greater than or at least equal to 3.5 percent, or 3.6 percent, or 3.7 percent, and in some cases may be less than 10 or 15 or 20 percent. In some embodiments, the second percentage is less than 2 percent, or less than 1.5 percent, or less than about 1 percent. In some embodiments, the first percentage is at least 3.7 percent and the second percentage is less than 1.5 percent. Having a large first percentage indicates that the optical film would produce a large variation in reflection band wavelengths if the thickness of the optical film were not varied to reduce or eliminate this variation. Having a small second percentage indicates that a significant portion of the variation has been eliminated.

In some embodiments, the absolute value of the difference between the first and second reflection band edge wavelengths is at least 12 nm, or at least 15 nm, and the absolute value of the difference between the first and third reflection band edge wavelengths is less than 6 nm or less than 5 nm.

The optical film may also have a second reflection band edge wavelength and a reflection band center wavelength that exhibit similar behavior as the first reflection band edge wavelength. In some embodiments, the optical film has a first reflection band center wavelength for light 502 incident on the lens at normal incidence at the first location 521, and has a second reflection band center wavelength for light 506 incident on the lens at an incidence angle $\alpha$, which may be 25 degrees, at the first location 521. The second reflection band center wavelength differs from the first reflection band center wavelength by a third percentage. The optical film also has a third reflection band center wavelength for light 504 incident on the lens at the incidence angle $\alpha$ at the second location 522. The third reflection band center wavelength differs from the first reflection band center wavelength by a fourth percentage. The fourth percentage may be less than one half (or less than one third or less than one fourth or less than one fifth) of the third percentage. In some embodiments, the absolute value of the difference between the first and second reflection band center wavelengths is at least 12 nm, or at least 15 nm, and the absolute value of the difference between the first and third reflection band center wavelengths is less than 6 nm or less than 5 nm.

In some embodiments, the incidence angle $\alpha$ used in defining the second and third reflection band center or edge wavelengths is 25 degrees. In some embodiments, the optical film has a fourth reflection band center or band edge wavelength at a 30 degree incidence angle at the first location 521 where the fourth reflection band center or band edge wavelength differs from the first reflection band center or band edge wavelength by a fifth percentage. The optical film also has a fifth reflection band center or band edge wavelength at a 30 degree incidence angle at a third location different from the first and second locations where the fifth reflection band center or band edge wavelength differs from the first reflection band center or band edge wavelength by a sixth percentage. The sixth percentage may be less than one half, or one third, or one fourth of the fifth percentage. The fourth and fifth reflection band center or band edge wavelengths are each short wavelength band edge wavelengths, or long wavelength band edge wavelengths, or reflection band center wavelengths.

In some embodiments, eyewear lens 500a includes a polymeric multilayer optical film having a reflection band (corresponding to band 301a in FIG. 3, for example) that has at least one reflection band edge. When an incidence position of a light ray that is incident on an outer surface 511 of the lens in air and that passes through the fixed point 525a proximate the lens opposite the outer surface 511 varies through a portion 523 of the outer surface 511 such that an incidence angle α of the light ray with the outer surface varies from zero degrees to 25 degrees, the eyewear lens provides a reflection band edge wavelength having a first maximum variation of less than 2.5 percent, or less than 2 percent or less than 1.5 percent, or less than 1 percent. The maximum variation of a wavelength through a portion of the lens may be understood to be the difference between the maximum and minimum of the wavelength in the portion divided by the minimum of the wavelength in the portion times 100 percent. In some embodiments, when the incidence angle varies from zero to 30 degrees, the reflection band edge wavelength has a second maximum variation of less than 3 percent, or less than 2.5 percent, or less than 2 percent, or less than 1.5 percent, or even less than about 1 percent. When the incidence angle varies from zero to 25 or 30 degrees, the incidence position may vary substantially continuously in a plane (e.g., the plane of FIG. 5) containing an arc length of the lens and containing the fixed point 525a.

In some embodiments, the thickness varies substantially continuously in at least a portion (e.g., portion 523) of the eyewear lens 500a. The thickness may substantially monotonically increase or substantially monotonically decrease in at least a portion of the lens 500a. Similarly, the reflection band edge wavelengths and/or the reflection band center wavelength may vary substantially continuously in at least a portion of the eyewear lens 500a, and may substantially monotonically increase or substantially monotonically decrease in a least a portion of the eyewear lens 500a. The portion over which the thickness or reflection band wavelengths vary continuously or monotonically may include an arc having a length of at least 1 cm, or at least 2 cm, or at least 4 cm, along which the wavelengths vary, for example, and the portion may have an area of at least 1 cm² or at least 4 cm², or at least 10 cm², for example. A thickness may be said to vary substantially continuously if the thickness not including any small local random variations (e.g., less than 1%) varies continuously. Similarly, a thickness may be said to vary substantially monotonically if the thickness not including any small local random variations (e.g., less than 1%) varies monotonically.

Any suitable eyewear lens geometry may be used. The lens may have a radius of curvature in a range of 50 mm to 200 mm, or in a range of 60 mm to 120 mm, for example. The radius of curvature of an eyewear lens is customarily described in terms of a base number or base curve number by the formula: radius of curvature in mm equals 0.53 divided by the base number times a thousand. For example, a base 6 lens has a radius of curvature of 88 mm and a base 8 lens has a radius of curvature of 66 mm. In some embodiments, first lens 500a (and similarly for second lens 500b) has a radius of curvature which is the distance between the lens 500a and the first center of curvature 527a.

In some embodiments, the first fixed point 525a is separated from the center of curvature 527a by at least half of the radius of curvature.

The lenses used for illustration in FIGS. 6-12 are base 6 lenses. The lenses have a 32 mm sphere center separation (the corresponding distance between the first and second centers of curvature 527a and 527b of the first and second lenses 500a and 500b is 32 mm) and an eye separation of 64 mm is assumed. This particular lens geometry was chosen for illustrative purposes only. It should be understood that any other suitable lens geometry could be chosen. In some embodiments, the eyewear lens may have a base curve number in the range of 6 to 9, or in the range of 8 to 9. An eyewear lens with a base curve of 9, for example, may be used in wrap-around style eyewear. Conventional polymeric multilayer optical films may exhibit large, undesired band-edge shifts with eye viewing angle when incorporated into such eyewear. The polymeric multilayer optical films of the present description may be particularly advantageous for such applications.

Figure 6:
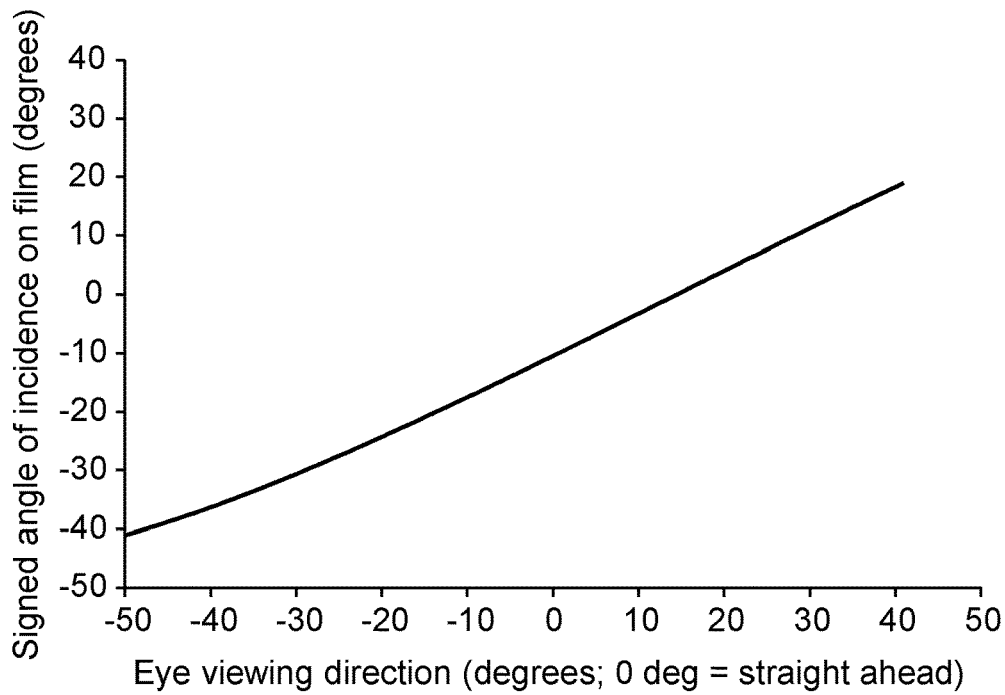
FIG. 6 is a graph of the signed angle of incidence of light on a film in an eyewear lens as a function of a viewing direction through the lens.

FIG. 6 is a graph of the signed angle of incidence of light on a film in an eyewear lens as a function of an eye viewing direction through the lens. As used herein, unless indicated differently, angle of incidence or incidence angle refers to the magnitude (zero to 90 degrees) between an incident light ray and a normal vector to a surface. In some cases it may be desired to keep track of a relative sign of the angle of incidence as a position on a lens varies in a plane, such as for example, in the plane of FIG. 5. In such cases, it may be useful to refer to the signed angle of incidence. For example, light ray 504 may be described as having an angle of incidence on the lens 500a of 25 degrees and as having a signed angle of incidence on the lens 500a of −25 degrees. In FIG. 6, an eye viewing direction of zero degrees corresponds to looking straight ahead and since the lens curves about the head somewhat (see, e.g., FIG. 5), the signed angle of incidence on the film is about −10 degrees when the user is looking straight ahead.

Figure 7:
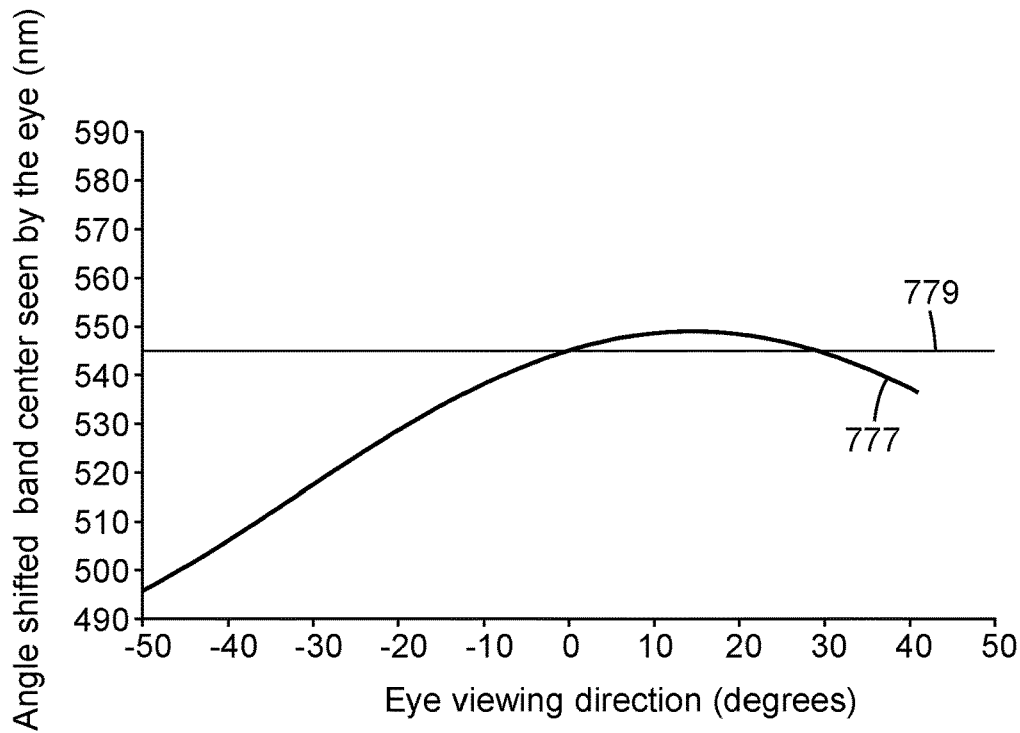
FIG. 7 is a graph of a reflection band center wavelength along a viewing direction through a lens as a function of the viewing direction.

FIG. 7 is a graph of a reflection band center wavelength 777 along an eye viewing direction through a lens as a function of the eye viewing direction. Since the angle of incidence varies with eye viewing direction (as illustrated in FIG. 6) and since the reflection band center wavelength depends of the angle of incidence (as illustrated in FIG. 4), the reflection band center wavelength varies with the eye viewing direction through the lens. The reflection band of the film utilized in FIG. 7 has a short wavelength band edge and a long wavelength band edge. Both the short and long wavelength band edges have a wavelength that varies with eye viewing direction similarly to the reflection band center wavelength illustrated in FIG. 7. Also shown in FIG. 7 is a target center wavelength 779 that may be desired in some embodiments. Target center wavelength 779 is independent of eye viewing direction.

In certain applications, the shift in the reflection band center wavelength or corresponding shifts in first or second reflection band edge wavelengths may be acceptable. In other applications, it may be desired to significantly reduce or eliminate such variation. For example, a film with a blocking band having a narrow bandwidth in a specific wavelength range may be used as colorblind corrective film as described elsewhere. In this case, a shift in the reflection band center wavelength could shift the band outside of the specific wavelength range needed resulting in poor performance of the film. Another example is films used in protective eyewear for lasers. In such cases in may be desired to have a band edge not shift with eye viewing direction so that the lens blocks hazardous laser light regardless of eye viewing direction.

Figure 8:
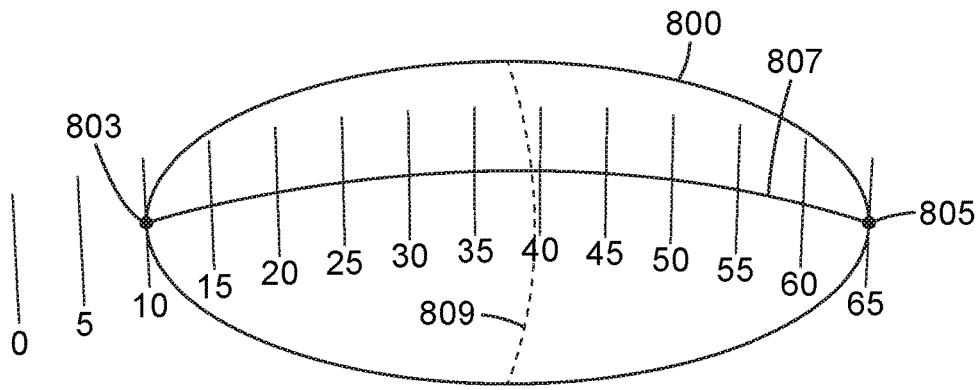
FIG. 8 is an illustration of a coordinate system along an arc length of a lens.

It may be more convenient to describe the reflection band center or edge wavelengths in terms of a distance along the lens rather than an eye viewing direction through the lens. FIG. 8 is an illustration of a coordinate system along an arc length of a lens 800. In the illustrated embodiment, the lens 800 has an arc length of 55 mm and the coordinate system has a zero point chosen to be the center of the eyes when the lens is worn. This zero point is 10 mm from a proximal edge 803 of the lens 800. Lens 800 also has a distal edge 805 opposite the proximal edge 803. The arc length is measured along an arc 807 from the proximal edge 803 to the distal edge 805. The arc 807 may be understood to be a geodesic curve of the outer surface of the lens 800. Also shown in FIG. 8 is arc 809 which is substantially orthogonal to arc 807.

Figure 9:
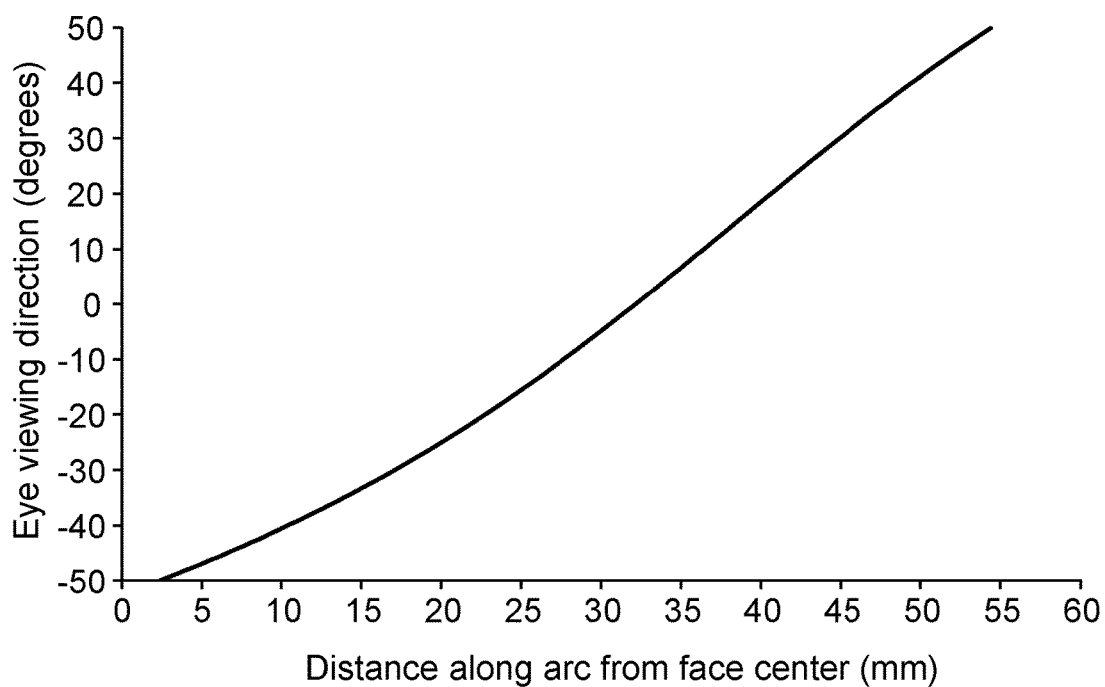
FIG. 9 is a graph of viewing direction through a lens as a function of distance along an arc length of the lens.
Figure 10:
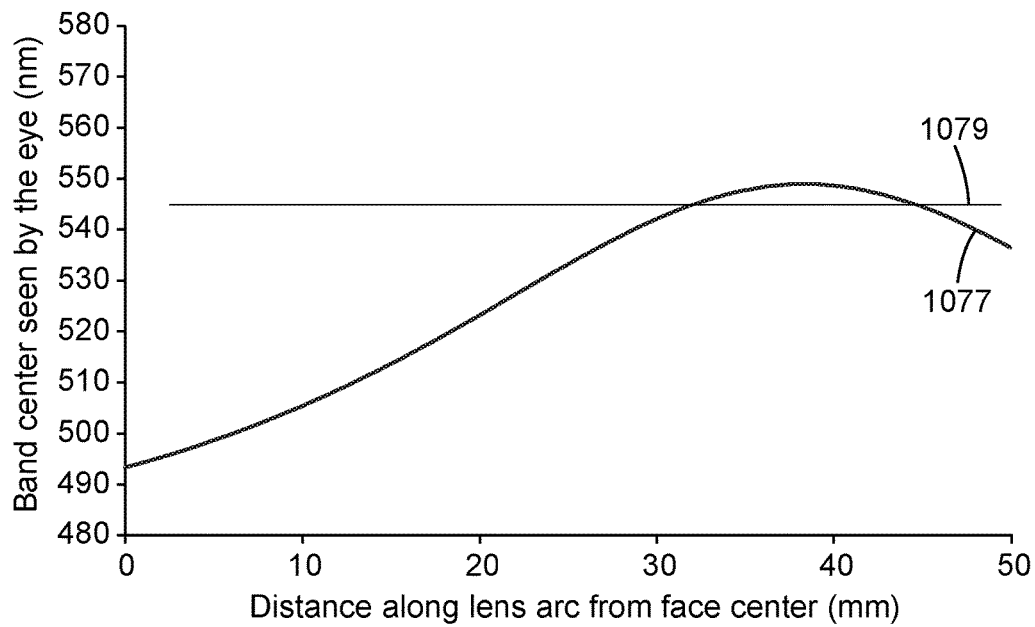
FIG. 10 is a graph of reflection band center wavelength along a viewing direction through a lens as a function of distance along an arc length of the lens.

FIG. 9 is a graph of eye viewing direction through a lens as a function of distance along an arc length (corresponding to a length along arc 807) of the lens. The plot of FIG. 9 can be combined with the plot of FIG. 7 to obtain the reflection band center wavelength as a function of distance along an arc of the lens. This is done in FIG. 10 which is a graph of reflection band center wavelength 1077 along an eye viewing direction through a lens as a function of distance along an arc length of the lens. Also shown in FIG. 10 is a target center wavelength 1079 that may be desired in some embodiments. Target center wavelength 1079 is independent of eye viewing direction.

Figure 11:
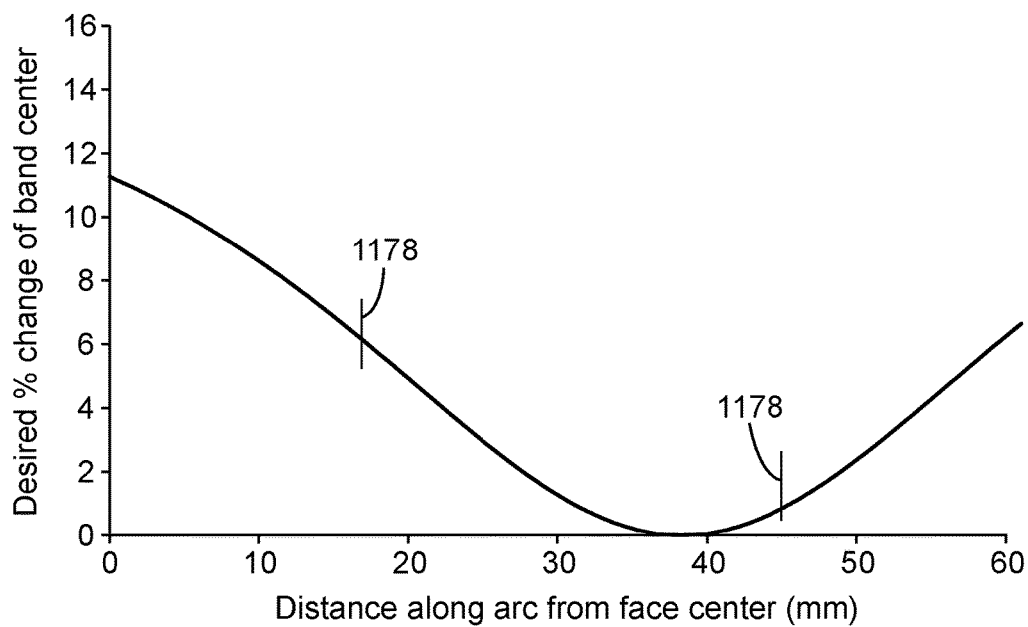
FIG. 11 is a graph of the percent change in a reflection band center wavelength needed to produce a reflection band center wavelength that is independent of a viewing direction through a lens as a function of distance along an arc length of the lens.
Figure 12:
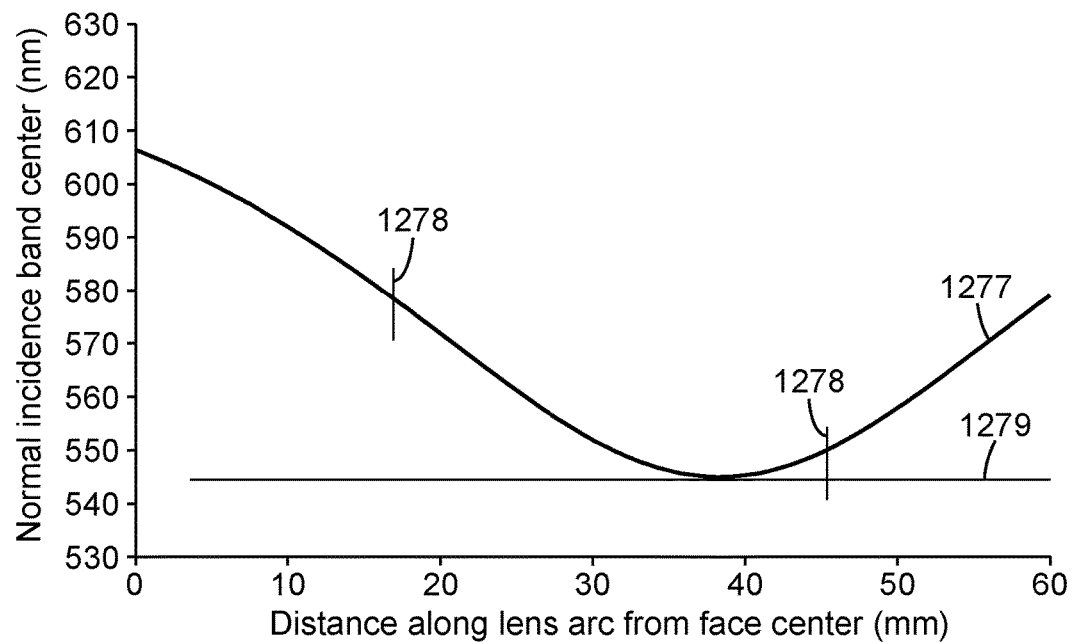
FIG. 12 is a graph of the normal incidence reflection band center wavelength needed to produce an actual incidence reflection band center wavelength that is independent of a viewing direction through a lens as a function of distance along an arc length of the lens.

From FIG. 10, the percentage shift needed to produce a constant reflection band center wavelength can be determined. This is shown in FIG. 11 which is a graph of the percent change in the reflection band center wavelength needed to result in a reflection band center wavelength that is independent of the eye viewing direction through a lens as a function of distance along an arc length of the lens. The distances 1178 corresponding to field of view angles of plus or minus 30 degrees are indicated. The desired percent change in the reflection band center wavelength is also a percent change desired in the thickness of the film since the reflection band center and edge wavelengths scale with thickness of the film. The normal incidence reflection band center wavelength can also be determined. This is shown in FIG. 12 which is a graph of the normal incidence reflection band center wavelength 1277 needed to produce an actual incidence reflection band center wavelength that is independent of an eye viewing direction through a lens as a function of distance along an arc length of the lens. The distances 1278 corresponding to field of view angles of plus or minus 30 degrees are indicated. Also shown in FIG. 12 is a target center wavelength 1279 that may be desired in some embodiments. Target center wavelength 1279 is independent of eye viewing direction.

Figure 13A:
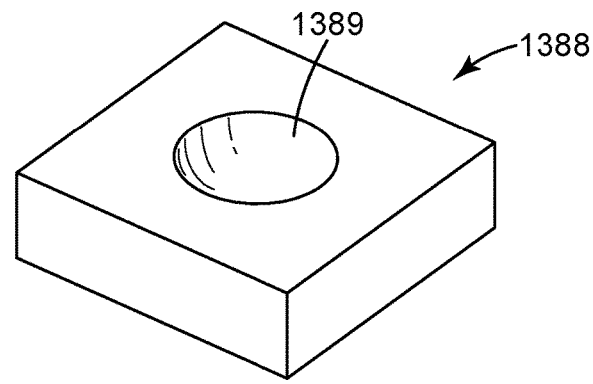
FIG. 13A is a schematic perspective view of a mold.
Figure 13B:
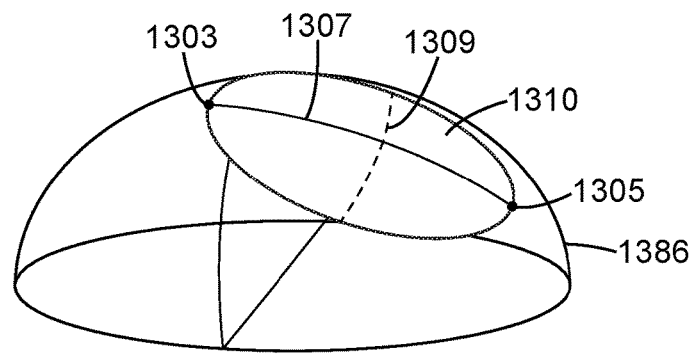
FIG. 13B is a perspective view of a thermoformed film or laminate.

Polymeric multilayer optical films having a desired position-dependent thickness can be made by thermoforming, for example. Using convex or concave molds, such as hemispherical or ellipsoidal shaped molds, for example, allows a desired variation in the film thickness to be obtained by using thermoforming process with suitably selected mold and film temperatures. Such a mold is illustrated in FIG. 13A which is a perspective view of mold 1388 having a concave hemispherical shaped cavity 1389. FIG. 13B shows film or laminate 1386 which is or which includes a multilayer optical film. Film or laminate 1386 may be a laminate having polycarbonate on each side of a multilayer optical film (e.g., a wafer with 0.1 mm-0.4 mm of polycarbonate on each side of the multilayer optical film, or a lens with 0.25 mm-2 mm of polycarbonate on each side of the multilayer optical film). The polycarbonate may have a same or different thickness on opposing sides of the lens. For example, the polycarbonate may be 2 mm on one side and 0.25 mm on the opposite side. FIG. 13B also shows portion 1310 of the film or laminate 1386 suitable for use in eyewear lenses. In some cases, the portion 1310 of the thermoformed film or laminate 1386 to be used in an eyewear lens is selected to provide the desired thickness profile. For example, the portion 1310 of the film or laminate 1386 may be thinner near edge 1303 than near edge 1305. The portion 1310 includes the apex (deepest point into the concave mold, in this case) of the inverted dome 1389 of the mold 1388. The portion 1310 of film or laminate 1386 may be thinnest in the region near the apex and thus by choosing the location of the film relative to the apex, a distribution of thicknesses can be obtained through the portion 1310. For example, by choosing the shape of the mold 1388, the location and orientation of the portion 1310 in the mold 1388, the percent change in the thickness of the thermoformed optical film as a function of position can be chosen to approximately follow the curve shown in FIG. 11.

In the embodiment illustrated in FIGS. 13A-13B, a concave mold is used and the area of the film or laminate 1386 nearest the apex is stretched the most and is therefore the thinnest. In other embodiments, a convex mold may be used. For example, a convex mold having a hemispherical dome can be used and a film or laminate can be formed over the dome. In this case, the film or laminate may be pinned at the apex and this may be the thickest region of the film or laminate after thermoforming. The film or laminate would stretch more and therefore become thinner away from the apex. A portion of the thermoformed film or laminate can be selected to give a desired thickness distribution. In some cases, the portion of the mold used to form the lens can be selected as follows. For a given mold and processing conditions, an optical film, or a laminate including an optical film, can be thermoformed and the thickness distribution through the optical film can be measured. The thickness can be measured, for example, by using a spectrometer to determine a reflection band edge wavelength as a function of position and then calculating the thickness from the wavelength. From this thickness distribution, a suitable portion of the optical film or optical film laminated with polycarbonate or other polymer can then be identified to give a thickness profile of the optical film approximating the curve shown in FIG. 11, for example, when expressed as a percentage.

The orientation of the portion 1310 of the film or laminate 1386 and the geometry of the mold 1388 (e.g., hemispherical) may be chosen so that the thickness of the film varies (e.g., substantially continuously) along arc 1307 between edges 1303 and 1305 and is substantially constant along the orthogonal arc 1309. Alternatively, the mold geometry or the orientation may be selected to give a desired thickness variation along arc 1309 as well.

In some embodiments, the resulting thickness of the film and/or a normal incidence reflection band edge wavelength and/or a normal incidence reflection band center wavelength substantially monotonically decreases in at least a portion of the polymeric multilayer optical film along an arc length (for example, over at least a 0.5 cm, or over at least a 1 cm, or over at least a 2 cm, or at least a 4 cm, or at least a 5 cm length of an arc length) from a first end of the portion closest to an edge of the lens to a second end of the portion opposite the first end.

The thermoforming process may utilize any suitable temperatures and dwell times. For example, in some embodiments, the mold temperature is in a range of 150° C. to 250° C. and a pre-heat dwell time of 5 seconds to 90 seconds or of 20 second to 60 seconds may be utilized. It has been found that using a smaller mold for a given base number allows the dwell time to be reduced. In addition, it has been found that using thinner polycarbonate outer layers also allows the dwell time to be reduced.

In some cases, removable outer laminates, such as vinyl or fluorocarbon films, for example, may be added to the polymeric multilayer optical film before thermoforming. Such outer laminates can allow a pre-oriented polymeric multilayer optical film to re-arrange itself after molding the film over the tool which may be a higher temperature than the glass transition temperature (Tg) of the outer laminate. The removable outer laminate may therefore be useful for achieving a controlled stretch, particularly when convex molds are used.

In some cases, a laminate including a polymeric multilayer optical film laminated between two sheets can be thermoformed and a wafer can be cut from a suitable location in the thermoformed laminate to produce a curved wafer including the optical film with a desired thickness distribution. Additional lens material can be added to the curved wafer in a separate injection molding step. For example, 0.25 mm thick polycarbonate sheets can be laminated to each side of a polymeric multilayer optical film using, for example, a 25 micrometer thick (or 15 to 50 micrometers thick) optically clear adhesive. The laminate can be thermoformed using a mold such as mold 1388. A curved wafer can then be cut from the thermoformed laminate and an injection molding process can be used to form a lens having the curved laminate between two curved polycarbonate shells. The resulting lens can have a thickness of greater than 2 mm, for example. Alternatively, a thicker laminate can be thermoformed to form a curved lens incorporating the optical film without an additional injection molding step. For example, polycarbonate sheets having a thickness in the range of 0.25 mm to 2.0 mm, for example, can be laminated to each side of a polymeric multilayer optical film using, for example, a 25 micrometer thick (or 15 to 50 micrometers thick) optically clear adhesive. The laminate can be thermoformed using a mold such as mold 1388. A curved lens can then be cut from the thermoformed laminate.

An alternative to selecting a suitable portion of a thermoformed optical filter to provide a desired thickness distribution, is to stretch an optical filter in the presence of a non-uniform (i.e., not constant) temperature distribution. Hotter portions of the filter will stretch and thin more than cooler portions of the filter and therefore a desired thickness profile can be achieved by suitably selecting a temperature distribution. This can be done by using spot heaters, for example, to control the temperature distribution. This allows a flat optical filter to be made. Alternatively, an optical filter having a non-uniform temperature profile can be stretched to give a flat or approximately flat optical filter with a non-uniform thickness profile which can then be thermoformed into a desired shape (e.g., a shape suitable for use in an eyewear lens). The initial non-uniform temperature profile can be adjusted and the portion of the thermoformed optical filter can be selected to give a desired thickness profile.

EXAMPLES

Example 1

A polymeric multilayer optical film was made with a stack of 275 individual microlayers alternating between PET and coPMMA polymer materials as generally described in PCT Publication No. WO 2014/110101 (Wold et al.). The layer thickness profile of the stack was tailored to produce a first-order reflection band in the infrared region of the spectrum. The $3^{rd}$ order harmonic of the IR reflection band was in the visible region near 550 nm and had a band width (FWHM) of about 40 nm.

The optical film was laminated between two 40 mil (1 mm) thick polycarbonate (available from McMaster-Carr, Sante Fe Springs, Calif.) sheets using 1 mil (0.025 mm) thick optically clear adhesive (3M™ Optically Clear Adhesive 8171 available from 3M Company, St. Paul, Minn.) between the layers. Two 5 mil (0.13 mm) thick PET films, each having a surface treatment on one side, was used to protect the laminate during the thermoforming process. Samples were tested with the PET films disposed with the surface treated sides facing towards or away from the laminate, and the orientation was found to not significantly affect the reflection band of the resulting thermoformed laminate. Other examples were made using protective films other than PET, such as polyethylene. Depending on the platen temperature and dwell time, using polyethylene films may provide better optical clarity than using PET film. The laminate was then thermoformed using a mold such as mold 1388 illustrated in FIG. 13. The thermal forming equipment used was similar to the IL 50 and IL 75 Accuform Series by Hytech Forming Systems (Phoenix, Ariz.). The mold was a base 6 mold obtained from Hytech Forming Systems and was bowl (inverse hemispherical dome) shaped with a depth of 35.4 mm and a radius of curvature of 88 mm. The mold included pin holes at the bottom of the bowl for applying an up-pressure throughout the pre-dwell period and for removing air when the laminate was forced into the mold.

During a 45 second pre-heat dwell time, a platen temperature of approximately 400° F. (204° C.), a mold (tool) temperature of approximately 100° F. (38° C.), and a pre-mold upward pressure of 80 psi (552 kPa) was used to heat the laminate. After the dwell time was complete, a downward pressure of 500 psi (3.45 MPa) was applied to the laminate to force it into the mold. After applying pressure for about 2 seconds the platen was raised and the laminate was removed from the mold.

A part of the laminate was cut out to facilitate measurement and the normal incidence reflection band center wavelength was measured approximately every 10 mm along an arc length of the part using a spectrometer. From the band center wavelength distribution, a portion of the thermoformed laminate was selected and was cut out using a Computerized Numerical Control (CNC) mill to obtain a portion suitable for use in eyewear.

Figure 14:
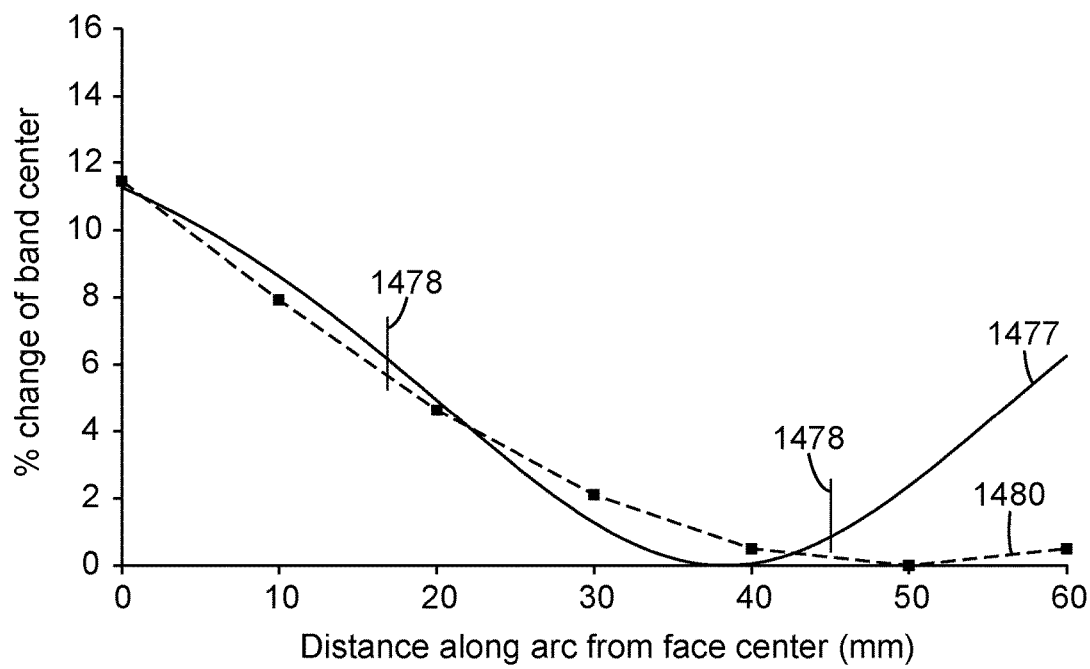
FIG. 14 is a graph of the percent change in a reflection band center wavelength needed to produce a reflection band center wavelength that is independent of a viewing direction through a lens and the percent change obtained in a sample lens as a function of distance along an arc length of the lens.

The reflection band center wavelength at normal incidence along an arc length of a portion of the eyewear leans was measured using a spectrometer. The percent change relative to a non-thermoformed film was determined. FIG. 14 is a graph of the experimental percent change 1480 and the needed percent change 1477 in the reflection band center wavelength to result in a reflection band center wavelength that is independent of the eye viewing direction through a lens as a function of distance along an arc length of the lens. The distances 1478 corresponding to field of view angles of plus or minus 30 degrees are indicated. The sample film gave a percent change reasonably close to the desired percent change through the view angles of plus or minus 30 degrees. The percent change in the reflection band center wavelength 1480 is also a percent change in the thickness of the film since the reflection band center and edge wavelengths scale with thickness of the film.

Examples 2-4

A thermoformed laminate was made as in Example 1, except the thickness of the polycarbonate sheets, the tool temperature, platen temperature and the dwell time were selected according to the following table.

| Example | Polycarbonate Thicknesses (millimeters) | Platen Temperature (° C.) | Tool (Mold) Temperature (° C.) | Dwell Time (seconds) |
| --- | --- | --- | --- | --- |
| 1 | 1 | 204 | 38 | 45 |
| 2 | 0.76 | 204 | 49 | 15 |
| 3 | 0.76 | 204 | 49 | 20 |
| 4 | 1 | 204 | 46 | 45 |

The reflection band center wavelength at normal incidence along an arc length of a portion of the laminates were measured using a spectrometer. In each case a portion of the thermoformed laminate had a reflection band center wavelength that varied with position along an arc length of the portion and that was suitable for use in an eyewear lens.

The following is a list of exemplary embodiments of the present description.

Embodiment 1 is an optical filter comprising a polymeric multilayer optical film, wherein the polymeric multilayer optical film has a reflection band having a first reflection band edge, the first reflection band edge having a location-dependent normal incidence first reflection band edge wavelength, wherein the first reflection band edge is, independent of location, one of a short wavelength band edge at a short wavelength side of the reflection band and a long wavelength band edge at a long wavelength side of the reflection band, and wherein the normal incidence first reflection band edge wavelength is a first wavelength at a first location and is a second wavelength at a second location different from the first location, the first wavelength higher than the second wavelength by at least 2 percent.

Embodiment 2 is the optical filter of embodiment 1, wherein the reflection band at the first location and at normal incidence has a width (FWHM) of 100 nm or less.

Embodiment 3 is the optical filter of embodiment 2, wherein the width is 60 nm or less.

Embodiment 4 is the optical filter of embodiment 2, wherein the width is 40 nm or less.

Embodiment 5 is the optical filter of embodiment 1, wherein the first reflection band edge is the long wavelength band edge and the first wavelength is greater than 1064 nm.

Embodiment 6 is the optical filter of embodiment 5, wherein the reflection band at normal incidence at the first location includes wavelengths at least from 793 nm to 1064 nm.

Embodiment 7 is the optical filter of embodiment 6, where the reflection band at normal incidence at the first location includes wavelengths at least from 760 nm to 1300 nm.

Embodiment 8 is the optical filter of embodiment 1, wherein the reflection band has a second band edge, the first band edge is the short wavelength band edge and the second band edge is the long wavelength band edge.

Embodiment 9 is the optical filter of embodiment 1, wherein the reflection band has a normal incidence reflection band center wavelength that is higher at the first location than at the second location by at least 2 percent.

Embodiment 10 is the optical filter of embodiment 9, wherein the normal incidence reflection band center wavelength is higher at the first location than at the second location by at least 3 percent.

Embodiment 11 is the optical filter of embodiment 9, wherein the normal incidence reflection band center wavelength is higher at the first location than at the second location by at least 4 percent.

Embodiment 12 is the optical filter of embodiment 1, wherein the first wavelength is higher than the second wavelength by at least 3 percent.

Embodiment 13 is the optical filter of embodiment 1, wherein the first wavelength is higher than the second wavelength by at least 4 percent.

Embodiment 14 is the optical filter of embodiment 1, wherein the normal incidence first reflection band edge wavelength substantially monotonically decreases in at least a portion of the polymeric multilayer optical film along an arc length from a first end of the portion closest to an edge of the lens to a second end of the portion opposite the first end.

Embodiment 15 is the optical filter of embodiment 14, wherein the normal incidence first reflection band edge wavelength substantially monotonically decreases over at least a 1 cm length of the arc length.

Embodiment 16 is the optical filter of embodiment 14, wherein the normal incidence first reflection band edge wavelength substantially monotonically decreases over at least a 2 cm length of the arc length.

Embodiment 17 is the optical filter of embodiment 14, wherein the normal incidence first reflection band edge wavelength substantially monotonically decreases over at least a 4 cm length of the arc length.

Embodiment 18 is the optical filter of embodiment 1, wherein the optical film has a location-dependent thickness that varies substantially continuously in at least a portion of the optical filter.

Embodiment 19 is the optical filter of embodiment 18, wherein the portion has an area of at least 1 cm$^2$.

Embodiment 20 is the optical filter of embodiment 19, wherein the area is at least 4 cm$^2$.

Embodiment 21 is the optical filter of embodiment 19, wherein the area is at least 10 cm$^2$.

Embodiment 22 is the optical filter of embodiment 1, wherein for at least one portion of the film at normal incidence, the reflection band has a width (FWHM) of 60 nm or less, the polymeric multilayer optical film has an average internal transmission from 420-680 nm of at least 50%, and has an average internal transmission of 10% or less over a 10 nm wide wavelength range that includes 550 nm and is associated with the reflection band.

Embodiment 23 is the optical filter of embodiment 22, wherein the average internal transmission over the 10 nm wide wavelength range is 2% or less.

Embodiment 24 is the optical filter of embodiment 22, wherein the average internal transmission over the 10 nm wide wavelength range is 1% or less.

Embodiment 25 is the optical filter of embodiment 1, wherein the first band edge is the long wavelength band edge, and wherein for at least some portions of the polymeric multilayer optical film at normal incidence, the long wavelength band edge is in a range from 420 to 440 nm, and the polymeric multilayer optical film has an average light transmission of less than 2% across the reflection band and transmits at least 80 percent of blue light at normal incidence having a wavelength that is 10 nm or greater than the long wavelength band edge.

Embodiment 26 is the optical filter of embodiment 1, wherein the reflection band has a second band edge, the first band edge is the short wavelength band edge and the second band edge is the long wavelength band edge, and wherein for at least some portions of the polymeric multilayer optical film at normal incidence, the short wavelength band edge is at about 400 nm or less, the long wavelength band edge is in a range from 420 to 440 nm, and the polymeric multilayer optical film has an average light transmission of less than 2% across the reflection band and transmits at least 80 percent of blue light having a wavelength that is 10 nm or greater than the long wavelength band edge.

Embodiment 27 is the optical filter of embodiment 1, wherein the reflection band has a second band edge, the first band edge is the short wavelength band edge and the second band edge is the long wavelength band edge, and wherein at least a portion of the polymeric multilayer optical film at normal incidence reflects at least 80 percent in a wavelength range from 440 nm to 480 nm and transmits greater than 50% of blue light at a wavelength of 10 nm longer than the long wavelength band edge and at a wavelength of 10 nm shorter than the short wavelength band edge.

Embodiment 28 is the optical filter of embodiment 1, wherein at least a portion of the polymeric multilayer optical film at normal incidence reflects at least 80 percent of infrared light in a wavelength range of 793 nm to 1064 nm.

Embodiment 29 is the optical filter of embodiment 28, wherein at least a portion of the polymeric multilayer optical film at normal incidence reflects at least 80 percent of light in a wavelength range of 770 nm to 1200 nm.

Embodiment 30 is an eyewear lens comprising the optical filter of embodiment 1.

Embodiment 31 is eyewear comprising:
a first eyewear lens comprising a first optical filter according to embodiment 1;
a second eyewear lens comprising a second optical filter according to embodiment 1; and
a frame, the frame having a first lens mounting portion and a second lens mounting portion proximate the first lens mounting portion, the first eyewear lens mounted on the first lens mounting portion and the second eyewear lenses mounted on the second lens mounting portion.

Embodiment 32 is an optical filter comprising a polymeric multilayer optical film, the film having a reflection band,
wherein the film has a first reflection band edge wavelength for light incident on the lens at normal incidence at a first location, and has a second reflection band edge wavelength for light incident on the lens at a 25 degree incidence angle at the first location, the second reflection band edge wavelength differing from the first reflection band edge wavelength by a first percentage;
wherein the film has a third reflection band edge wavelength for light incident on the lens at a 25 degree incidence angle at a second location different from the first location, the third reflection band edge wavelength differing from the first reflection band edge wavelength by a second percentage being less than one half of the first percentage;
and wherein each of the first, second and third reflection band edge wavelengths are wavelengths of a short wavelength band edge at a short wavelength side of the reflection band or each of the first, second and third reflection band edge wavelengths are wavelengths of a long wavelength band edge at a long wavelength side of the reflection band.

Embodiment 33 is the optical filter of embodiment 32, wherein the first percentage is greater than 3.5 percent.

Embodiment 34 is the optical filter of embodiment 33, wherein the first percentage is at least 3.7 percent.

Embodiment 35 is the optical filter of embodiment 32, wherein the second percentage is less than 2 percent.

Embodiment 36 is the optical filter of embodiment 32, wherein the first percentage is at least 3.7 percent and the second percentage is less than 1.5 percent.

Embodiment 37 is the optical filter of embodiment 36, wherein the second percentage is less than about 1 percent.

Embodiment 38 is the optical filter of embodiment 32, wherein the second percentage is less than one third of the first percentage.

Embodiment 39 is the optical filter of embodiment 32, wherein the second percentage is less than one fourth of the first percentage.

Embodiment 40 is the optical filter of embodiment 32,
wherein the optical film has a first reflection band center wavelength for light incident on the lens at normal incidence at the first location, and has a second reflection band center wavelength for light incident on the lens at a 25 degree incidence angle at the first location, the second reflection band center wavelength differing from the first reflection band center wavelength by a third percentage, and
wherein the optical film has a third reflection band center wavelength for light incident on the lens at a 25 degree incidence angle at the second location, the third reflection band center wavelength differing from the first reflection band center wavelength by a fourth percentage being less than one half of the third percentage.

Embodiment 41 is the optical filter of embodiment 40, wherein the third percentage is at least 3.7 percent.

Embodiment 42 is the optical filter of embodiment 41, wherein the fourth percentage is less than about 1 percent.

Embodiment 43 is the optical filter of embodiment 40, wherein the fourth percentage is less than one fourth of the third percentage.

Embodiment 44 is the optical filter of embodiment 40, wherein an absolute value of a difference between the first and second reflection band center wavelengths is at least 12 nm and an absolute value of a difference between the first and third reflection band center wavelengths is less than 6 nm.

Embodiment 45 is the optical filter of embodiment 40, wherein an absolute value of a difference between the first and second reflection band center wavelengths is at least 15 nm and an absolute value of a difference between the first and third reflection band center wavelengths no greater than about 5 nm.

Embodiment 46 is the optical filter of embodiment 40, wherein the optical film has a fourth reflection band center wavelength at a 30 degree incidence angle at the first location, the fourth reflection band center wavelength differing from the first reflection band center wavelength by a fifth percentage, and the optical film has a fifth reflection band center wavelength at a 30 degree incidence angle at a third location different from the first and second locations, the fifth reflection band center wavelength differing from the first reflection band center wavelength by a sixth percentage being less than one half of the fifth percentage.

Embodiment 47 is the optical filter of embodiment 46, wherein the sixth percentage is less than one third of the fifth percentage.

Embodiment 48 is the optical filter of embodiment 46, wherein the sixth percentage is less than one fourth of the fifth percentage.

Embodiment 49 is the optical filter of embodiment 32, wherein each of the first, second and third reflection band edge wavelengths are wavelengths of the long wavelength band edge and each of the first and third reflection band edge wavelengths is greater than 1064 nm.

Embodiment 50 is the optical filter of embodiment 49, wherein the reflection band at normal incidence at the first location includes wavelengths at least from 793 nm to 1064 nm.

Embodiment 51 is the optical filter of embodiment 50, where the reflection band at normal incidence at the first location includes wavelengths at least from 760 nm to 1300 nm.

Embodiment 52 is the optical filter of embodiment 32, where the reflection band at normal incidence at the first location has a width (FWHM) of 60 nm or less and includes 550 nm.

Embodiment 53 is the optical filter of embodiment 32, where the reflection band at normal incidence at the first location has a width (FWHM) of 40 nm or less and includes 550 nm.

Embodiment 54 is the optical filter of embodiment 32, wherein when a first light ray is incident at the first location at normal incidence from an outer surface of the lens, it passes through a point proximate the lens opposite the outer surface; and when a second light ray is incident at the second location from the outer surface of the lens at a 25 degree incidence angle, it passes through the point.

Embodiment 55 is an eyewear lens comprising the optical filter of embodiment 32.

Embodiment 56 is eyewear comprising:
a first eyewear lens comprising a first optical filter according to embodiment 32,
a second eyewear lens comprising a second optical filter according to embodiment 32, and
a frame, the frame having a first lens mounting portion and a second lens mounting portion proximate the first lens mounting portion, the first eyewear lens mounted on the first lens mounting portion and the second eyewear lenses mounted on the second lens mounting portion.

Embodiment 57 is an optical filter comprising a polymeric multilayer optical film having a reflection band, wherein when an incidence position of a light ray that is incident on an outer surface of the lens in air and that passes through a fixed point proximate the lens opposite the outer surface varies through a portion of the outer surface such that an incidence angle of the light ray with the outer surface varies from zero degrees to 25 degrees, the optical filter provides a reflection band edge wavelength having a first maximum variation of less than 2.5 percent.

Embodiment 58 is the optical filter of embodiment 57, wherein the first maximum variation is less than 2 percent.

Embodiment 59 is the optical filter of embodiment 57, wherein the first maximum variation is less than 1.5 percent.

Embodiment 60 is the optical filter of embodiment 57, wherein the first maximum variation is less than 1 percent.

Embodiment 61 is the optical filter of embodiment 57, wherein when the incidence angle varies from zero degrees to 30 degrees, the reflection band edge wavelength has a second maximum variation of less than 3 percent.

Embodiment 62 is the optical filter of embodiment 61, wherein the second maximum variation is less than 2.5 percent.

Embodiment 63 is the optical filter of embodiment 61, wherein the second maximum variation is less than 2 percent.

Embodiment 64 is the optical filter of embodiment 61, wherein the second maximum variation is less than 1.5 percent.

Embodiment 65 is the optical filter of embodiment 57, wherein the lens has a radius of curvature and the fixed point is separated from a center of curvature of the lens by at least half of the radius of curvature.

Embodiment 66 is the optical filter of embodiment 57, wherein the incidence position varies substantially continuously in a plane containing an arc length of the lens and containing the fixed point.

Embodiment 67 is the optical filter of embodiment 57, wherein when the incidence angle of the light ray with the outer surface varies from zero degrees to 25 degrees, the optical filter provides a reflection band center wavelength having a third maximum variation of less than 2.5 percent.

Embodiment 68 is the optical filter of embodiment 67, wherein the third maximum variation is less than 1 percent.

Embodiment 69 is the optical filter of embodiment 57, wherein when the incidence angle of the light ray with the outer surface varies from zero degrees to 25 degrees, a wavelength of 550 nm remains in the reflection band and a width (FWHM) of the reflection band remains no more than 60 nm.

Embodiment 70 is the optical filter of embodiment 57, wherein when the incidence angle of the light ray with the outer surface varies from zero degrees to 25 degrees, a wavelength of 550 nm remains in the reflection band and a width (FWHM) of the reflection band remains no more than 40 nm.

Embodiment 71 is the optical filter of embodiment 57, wherein when the incidence angle of the light ray with the outer surface varies from zero degrees to 25 degrees, the reflection band edge wavelength remains greater than 1064 nm.

Embodiment 72 is the optical filter of embodiment 57, wherein when the incidence angle of the light ray with the outer surface varies from zero degrees to 25 degrees, wavelengths at least from 793 nm to 1064 nm remain in the reflection band.

Embodiment 73 is eyewear comprising a first eyewear lens, the first eyewear lens comprising an optical filter according to embodiment 57.

Embodiment 74 is the eyewear of embodiment 73 configured such that when worn, the fixed point is a center of rotation of an eye.

Embodiment 75 is eyewear comprising:
a first eyewear lens comprising a first optical filter according to embodiment 57;
a second eyewear lens comprising a second optical filter according to embodiment 57; and
a frame, the frame having a first lens mounting portion and a second lens mounting portion proximate the first lens mounting portion, the first eyewear lens mounted on the first lens mounting portion and the second eyewear lenses mounted on the second lens mounting portion.

Embodiment 76 is an eyewear lens comprising the optical filer of any of embodiments 1 to 29 or any of embodiments 32 to 54 or any of embodiments 57 to 72.

Embodiment 77 is the eyewear lens of embodiment 76 having a base curve number from 6 to 9.

Embodiment 78 is the eyewear lens of embodiment 77 having a base curve number from 8 to 9.

Embodiment 79 is a face-shield comprising an optical filter according to any of embodiments 1 to 29 or any of embodiments 32 to 54 or any of embodiments 57 to 72.

Embodiment 80 is goggles comprising an optical filter according to any of embodiments 1 to 29 or any of embodiments 32 to 54 or any of embodiments 57 to 72.

Embodiment 81 is a head mounted display comprising an optical filter according to any of embodiments 1 to 29 or any of embodiments 32 to 54 or any of embodiments 57 to 72.

Embodiment 82 is a machine vision system comprising an optical detector, the optical detector comprising an optical filter according to any of embodiments 1 to 29 or any of embodiments 32 to 54 or any of embodiments 57 to 72.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An optical filter comprising a polymeric multilayer optical film, wherein the polymeric multilayer optical film has a reflection band having a first reflection band edge, the first reflection band edge having a location-dependent normal incidence first reflection band edge wavelength, wherein the first reflection band edge is, independent of location, one of a short wavelength band edge at a short wavelength side of the reflection band and a long wavelength band edge at a long wavelength side of the reflection band, and wherein the normal incidence first reflection band edge wavelength is a first wavelength at a first location and is a second wavelength at a second location different from the first location, the first wavelength higher than the second wavelength by at least 2 percent.

2. The optical filter of claim 1, wherein the reflection band has a normal incidence reflection band center wavelength that is higher at the first location than at the second location by at least 2 percent.

3. The optical filter of claim 1, wherein the normal incidence first reflection band edge wavelength substantially monotonically decreases in at least a portion of the polymeric multilayer optical film along an arc length from a first end of the portion closest to an edge of the polymeric multilayer optical film to a second end of the portion opposite the first end.

4. The optical filter of claim 1, wherein for at least one portion of the film at normal incidence, the reflection band has a width (FWHM) of 60 nm or less, the polymeric multilayer optical film has an average internal transmission from 420-680 nm of at least 50%, and has an average internal transmission of 10% or less over a 10 nm wide wavelength range that includes 550 nm and is associated with the reflection band.

5. The optical filter of claim 1, wherein the first band edge is the long wavelength band edge, and wherein for at least some portions of the polymeric multilayer optical film at normal incidence, the long wavelength band edge is in a range from 420 to 440 nm, and the polymeric multilayer optical film has an average light transmission of less than 2% across the reflection band and transmits at least 80 percent of blue light at normal incidence having a wavelength that is 10 nm or greater than the long wavelength band edge.

6. The optical filter of claim 1, wherein the reflection band has a second band edge, the first band edge is the short wavelength band edge and the second band edge is the long wavelength band edge, and wherein for at least some portions of the polymeric multilayer optical film at normal incidence, the short wavelength band edge is at about 400 nm or less, the long wavelength band edge is in a range from 420 to 440 nm, and the polymeric multilayer optical film has an average light transmission of less than 2% across the reflection band and transmits at least 80 percent of blue light having a wavelength that is 10 nm or greater than the long wavelength band edge.

7. The optical filter of claim 1, wherein the reflection band has a second band edge, the first band edge is the short wavelength band edge and the second band edge is the long wavelength band edge, and wherein at least a portion of the polymeric multilayer optical film at normal incidence reflects at least 80 percent in a wavelength range from 440 nm to 480 nm and transmits greater than 50% of blue light at a wavelength of 10 nm longer than the long wavelength band edge and at a wavelength of 10 nm shorter than the short wavelength band edge.

8. Eyewear comprising:
a first eyewear lens comprising a first optical filter according to claim 1;
a second eyewear lens comprising a second optical filter according to claim 1; and
a frame, the frame having a first lens mounting portion and a second lens mounting portion proximate the first lens mounting portion, the first eyewear lens mounted on the first lens mounting portion and the second eyewear lenses mounted on the second lens mounting portion.

9. A head mounted display comprising an optical filter according to claim 1.

10. A machine vision system comprising an optical detector, the optical detector comprising an optical filter according to claim 1.

11. An optical filter comprising a polymeric multilayer optical film, the film having a reflection band,
wherein the film has a first reflection band edge wavelength for light incident on the film at normal incidence at a first location, and has a second reflection band edge wavelength for light incident on the film at a 25 degree incidence angle at the first location, the second reflection band edge wavelength differing from the first reflection band edge wavelength by a first percentage;
wherein the film has a third reflection band edge wavelength for light incident on the film at a 25 degree incidence angle at a second location different from the first location, the third reflection band edge wavelength differing from the first reflection band edge wavelength by a second percentage being less than one half of the first percentage; and
wherein each of the first, second and third reflection band edge wavelengths are wavelengths of a short wavelength band edge at a short wavelength side of the reflection band or each of the first, second and third reflection band edge wavelengths are wavelengths of a long wavelength band edge at a long wavelength side of the reflection band.

12. The optical filter of claim 11,
wherein the optical film has a first reflection band center wavelength for light incident on the optical film at normal incidence at the first location, and has a second reflection band center wavelength for light incident on the optical film at a 25 degree incidence angle at the first location, the second reflection band center wavelength differing from the first reflection band center wavelength by a third percentage, and
wherein the optical film has a third reflection band center wavelength for light incident on the optical film at a 25 degree incidence angle at the second location, the third reflection band center wavelength differing from the first reflection band center wavelength by a fourth percentage being less than one half of the third percentage.

13. The optical filter of claim 12, wherein an absolute value of a difference between the first and second reflection band center wavelengths is at least 12 nm and an absolute value of a difference between the first and third reflection band center wavelengths is less than 6 nm.

14. The optical filter of claim 12, wherein the optical film has a fourth reflection band center wavelength at a 30 degree incidence angle at the first location, the fourth reflection band center wavelength differing from the first reflection band center wavelength by a fifth percentage, and the optical film has a fifth reflection band center wavelength at a 30 degree incidence angle at a third location different from the first and second locations, the fifth reflection band center wavelength differing from the first reflection band center wavelength by a sixth percentage being less than one half of the fifth percentage.

15. The optical filter of claim 11, wherein when a first light ray is incident at the first location at normal incidence from an outer surface of the optical filter, it passes through a point proximate the optical filter opposite the outer surface; and when a second light ray is incident at the second location from the outer surface of the optical filter at a 25 degree incidence angle, it passes through the point.

16. Eyewear comprising:
a first eyewear lens comprising a first optical filter according to claim 11,
a second eyewear lens comprising a second optical filter according to claim 11, and
a frame, the frame having a first lens mounting portion and a second lens mounting portion proximate the first lens mounting portion, the first eyewear lens mounted on the first lens mounting portion and the second eyewear lenses mounted on the second lens mounting portion.

17. An optical filter comprising a polymeric multilayer optical film having a reflection band, wherein when an incidence position of a light ray that is incident on an outer surface of the optical filter in air and that passes through a fixed point proximate the optical filter opposite the outer surface varies through a portion of the outer surface such that an incidence angle of the light ray with the outer surface varies from zero degrees to 25 degrees, the optical filter provides a reflection band edge wavelength having a first maximum variation of less than 2.5 percent.

18. The optical filter of claim 17, wherein the optical filter has a radius of curvature and the fixed point is separated from a center of curvature of the optical filter by at least half of the radius of curvature.

19. The optical filter of claim 17, wherein when the incidence angle of the light ray with the outer surface varies from zero degrees to 25 degrees, the optical filter provides a reflection band center wavelength having a third maximum variation of less than 2.5 percent.

20. Eyewear comprising a first eyewear lens, the first eyewear lens comprising an optical filter according to claim 17, the eyewear configured such that when worn, the fixed point is a center of rotation of an eye.

* * * * *

UNITED STATES PATENT AND TRADEMARK OFFICE
CERTIFICATE OF CORRECTION

PATENT NO. : 10,444,546 B2
APPLICATION NO. : 15/754419
DATED : October 15, 2019
INVENTOR(S) : Chad Wold Page 1 of 1

It is certified that error appears in the above-identified patent and that said Letters Patent is hereby corrected as shown below:

In the Specification

Column 11
Line 22, delete "$(n_h+n_1)$" and insert -- $(n_h-n_1)/(n_h+n_1)$ --, therefor.
Line 35, delete "$n_n$" and insert -- $n_h$ --, therefor.

Signed and Sealed this
Twelfth Day of May, 2020

Andrei Iancu
*Director of the United States Patent and Trademark Office*